United States Patent [19]

Grollier et al.

[11] 4,295,848

[45] Oct. 20, 1981

[54] COMPOSITION FOR HAIR DYEING WHICH CONTAINS A PARA BASE AND AN ORTHO BASE

[75] Inventors: Jean F. Grollier, Paris; Andree Bugaut, Boulogne-Billancourt; Patrick Andrillon, Aulnay-sous-Bois; Chantal Fourcadier, Paris, all of France

[73] Assignee: L'Oreal, Paris, France

[21] Appl. No.: 201,505

[22] Filed: Oct. 29, 1980

Related U.S. Application Data

[62] Division of Ser. No. 27,363, Apr. 5, 1979.

[30] Foreign Application Priority Data

Apr. 6, 1980 [FR] France .................................. 78 10278

[51] Int. Cl.$^3$ ..................... C07C 50/80; C07C 119/12
[52] U.S. Cl. .......................................... 8/421; 8/410; 8/412; 260/396 N; 546/1
[58] Field of Search ............... 260/396 N; 8/412, 410, 8/421; 252/8.8

[56] References Cited

U.S. PATENT DOCUMENTS

| | | | |
|---|---|---|---|
| 2,895,826 | 7/1959 | Salminen et al. | 260/396 N |
| 3,884,627 | 5/1975 | Brody et al. | 8/406 |
| 3,961,879 | 6/1976 | Bugaut et al. | 8/409 |
| 3,970,423 | 7/1976 | Brody | 8/406 |
| 4,212,645 | 7/1980 | Leon et al. | 8/406 |
| 4,221,729 | 9/1980 | Kalopissis et al. | 260/396 N |

*Primary Examiner*—A. Lionel Clingman
*Attorney, Agent, or Firm*—Fleit & Jacobson

[57] ABSTRACT

The invention relates to compositions intended for dyeing keratin fibers which contain, as the only oxidative dyestuffs, oxidative dyestuff precursors of the para type and of the ortho type, at least one said precursor of the para type being an aromatic diamine, or specified formula or a specified bis-condensed precursor and at least one said precursor of the ortho type which is an ortho-aminophenol, ortho-diphenol, ortho-phenylenediamine or a derivative thereof.

4 Claims, No Drawings

COMPOSITION FOR HAIR DYEING WHICH CONTAINS A PARA BASE AND AN ORTHO BASE

This is a divisional of application Ser. No. 27,363 filed Apr. 5, 1979.

DESCRIPTION

The present invention relates to compositions which are intended for use in hair dyeing and contain para and ortho oxidative dyestuffs, and to a hair dyeing process.

It is well known to dye keratin fibres, and in particular human hair, with oxidative dyestuffs. Oxidative dyestuffs are generally aromatic compounds of the diamine, aminophenol or phenol type; these are well known in the state of the art. These compounds are not generally dyestuffs in themselves but are converted to dyestuffs by condensation in an oxidising medium.

Amongst oxidative dyestuffs, a distinction is made between, on the one hand, the oxidative dyestuff precursors of the para type, which are generally diamines and aminophenols in which the functional groups are in the para position relative to one another, and the oxidative dyestuff precursors of the ortho type, and, on the other hand, compounds referred to as modifiers, toners or couplers, which compounds are so-called meta derivatives, in particular m-diamines, m-aminophenols and m-diphenols, as well as phenols.

These oxidative dyestuff precursors are generally used with couplers for the purpose of obtaining a variety of colorations.

Although some of the abovementioned oxidative dyestuff precursors of the para type have for many years been recommended for use in hair dyes, it has not been possible to use them satisfactorily, in particular in conventional systems employing a coupler, because of their lack of strength, and the lack of selectivity of the resulting shades with respect to keratin fibres.

It is well known that selectivity is a significant problem, in practice, in the field of hair dyeing because of the different sensitisation to which the hair can be subjected. In fact, the hairdresser is generally confronted with hair of which the sensitisation is virtually zero for the freshly grown roots, strong for parts which have previously undergone coloration, bleaching or permanent waving, and very strong for the tips which have undergone several of these treatments and which are exposed daily to the action of light and adverse weather conditions. This problem is particularly significant for the so-called para oxidative bases in which one of the nitrogen atoms is monosubstituted or disubstituted, and also for the para-phenylenediamines in which the nitrogen atom is unsubstituted but in which the aromatic ring is very hindered.

We have now discovered, according to the present invention, that it is possible substantially to increase the strength of coloration of these bases by using them in association with certain oxidative dyestuff precursors of the ortho type, which are chosen, in particular, from ortho-aminophenols which are optionally substituted on the nitrogen atom, ortho-diphenols and ortho-phenylenediamines, and by avoiding, initially at least, any competition with conventional couplers such as the m-aminophenols or m-diamines.

We have discovered, inter alia, that the association of certain para-phenylenediamines with certain oxidative dyestuff precursors of the ortho type makes it possible, surprisingly, to obtain a strong coloration which is not simply the combinations of the colorations which the para base and which the ortho compound by themselves are capable of imparting. The abovementioned association leads to dyes which are very harmless and which possess, in particular, good resistance to external agents such as light, adverse weather conditions or washing.

We have also discovered that, surprisingly, the association of oxidative dyestuff precursors of the para type with, in particular, ortho-aminophenol leads, after penetration into the keratin fibre and in situ oxidation, to the formation of a compound containing three aromatic nuclei, this compound hereafter being referred to as a "trinuclear compound".

Finally, we have discovered that, by using an association of this kind in accordance with a two-stage dyeing process, it is possible to obtain a good uniformity of the coloration.

The present invention provides a composition suitable for dyeing keratin fibres, and in particular human hair, which comprises only, as oxidative dyestuff, an oxidative dyestuff precursor of the para type and of the ortho type, (i.e. the composition does not contain any coupler), (a) at least one of these oxidative dyestuff precursors being of the para type, and is:
a compound corresponding to the formula:

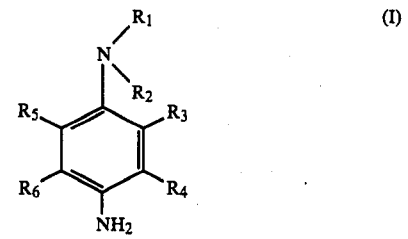

in which: $R_1$ and $R_2$ both denote a hydrogen atom, and at least two of the substituents $R_3$, $R_4$, $R_5$ and $R_6$ are not hydrogen and denote a lower alkyl or lower alkoxy group; or one of $R_1$ and $R_2$ is hydrogen and the other is not hydrogen, it being an alkyl group which contains a chain oxygen atom and is substituted by a hydroxyl group, or an alkyl group substituted by an acylamino, ureido, mesylamino or furfuryl group or by a sulphonamido group which is optionally substituted by one or two lower alkyl groups, if the aromatic nucleus is unsubstituted (i.e. $R_3$, $R_4$, $R_5$ and $R_6$, are all hydrogen) or is substituted by a halogen atom or a lower alkyl group i.e. at least one of $R_3$, $R_4$, $R_5$ and $R_6$ is a halogen atom or a lower alkyl group, the remainder being hydrogen, or, alternatively, one of $R_1$ and $R_2$ denotes a lower alkyl group which is optionally substituted by a hydroxyl, alkoxy or tetrahydrofurfuryl group, $R_3$ denotes a lower alkyl group, a halogen atom or a lower alkoxy group, $R_4$ denotes hydrogen, or a halogen atom if $R_3$ denotes hydrogen, and $R_5$ and $R_6$ denote hydrogen; $R_3$ being preferably not alkyl if $R_1$ or $R_2$ denotes alkyl or alkyl substituted by OH; or $R_1$ and $R_2$ are both different from hydrogen, $R_1$ being hyroxyalkyl or alkyl and $R_2$ denotes hydroxyalkyl, or alkyl substituted by an acylamino, mesylamino, carbamyl, sulphonamido or piperidino group, it being possible for $R_1$ and $R_2$ to form, together with the notrogen atom to which they are bonded, a piperidino or morpholino group, and the aromatic nucleus is unsubstituted (i.e. R$_3$, R$_4$, R$_5$ and R$_6$ are all hydrogen) or substituted by a lower alkyl group or a halogen atom (i.e. at least one of R$_3$, R$_4$, R$_5$ and R$_6$ is a lower alkyl group or a halogen atom, the remainder being hydrogen), or R$_1$ and R$_2$ both denote an alkyl group, R$_4$ denotes a halogen atom or an alkyl or alkoxy group, and R$_3$, R$_5$ and R$_6$ are hydrogen;

or a bis-condensed precursor which is a N,N'-diarylalkylenediamines in which the aryl groups are substituted in the para position by an OH or amino group which is optionally substituted by an alkyl group, it being possible for these amines themselves to be substituted by an alkyl, hydroxyalkyl or aminoalkyl group, such as described in French Patent No. 2,016,123, and also their salts; and (b) at least one of the oxidative dyestuff precursors being of the ortho type and is an ortho-aminophenol, orthodiphenol or ortho-phenylenediamine, in which compounds the aromatic nucleus is optionally substituted, e.g. by a lower alkyl or lower alkoxy group, which is located so that the 4- and 5-positions, relative to the OH group (if any), remain free, and in which compounds the nitrogen atom of one of the amino groups is optionally substituted by an alkyl group which is itself optionally substituted by a hydroxyl or alkoxy group, and also the cosmetically acceptable salts of these precursors.

The preferred oxidative dyestuff precursors of the ortho type are the ortho-diphenol, the ortho-phenylenediamines and ortho-aminophenols in which the aromatic nucleus is substituted by, for example, alkyl or alkoxy, it being possible for the nitrogen atom of the ortho-aminophenols or of the ortho-phenylenediamine to be optionally substituted by an alkyl group which is optionally substituted by an alkoxy or hydroxy group.

In the abovementioned formulae, the term lower alkyl group is used herein to mean a group having 1 to 6 carbon atoms and preferably a methyl, ethyl, propyl or butyl group. Halogen preferably denotes a chlorine atom. Alkoxy preferably denotes a group having 1 to 6 carbon atoms, such as methoxy, ethoxy or propoxy.

The oxidative dyestuff precursors of the para type which are preferred are chosen from amongst: 2,3,5,6-tetramethyl-p-phenylenediamine, 2,6-dimethyl-p-phenylenediamine, 2-methyl-5-methoxy-p-phenylenediamine, 2,6-dimethyl-5-methoxy-p-phenylenediamine, 4-amino-N-[β-(β'-hydroxyethoxy)-ethyl]-aniline, 4-amino-N-(β-acetylaminoethyl)-aniline, 4-amino-N-(β-mesylaminoethyl)-aniline, 4-amino-N-(β-sulphonamidoethyl)-aniline, 4-amino-N-[β-(diethylsulphonamido)-ethyl]-aniline, 4-amino-(N-furfuryl)-aminoaniline, 2-methyl-4-amino-N-methylaniline, 2-chloro-4-amino-N-methylaniline, 3-chloro-4-amino-N-methylaniline, 2-methoxy-4-amino-N-methylaniline, 2-chloro-4-amino-N-ethylaniline, 2-chloro-4-amino-N-butylaniline, 2-methyl-4-amino-N-(β-hydroxyethyl)-aniline, 2-methyl-4-amino-N-(β-methoxyethyl)-aniline and 2-chloro-4-amino-N-(β-methoxyethyl)-aniline, 4-N-ethyl-N-(β-hydroxyethyl)-aminoaniline, 2-methyl-4-amino-N-(β-acetylaminoethyl)-aniline, 2-chloro-4-amino-N-(β-acetylaminoethyl)-aniline, 2-methyl-4-amino-N-(β-ureidoethyl)-aniline, 2-chloro-4-amino-N-(β-ureidoethyl)-aniline, 2-methyl-4-amino-N-(β-mesylaminoethyl)-aniline, 2-chloro-4-amino-N-(β-mesylaminoethyl)-aniline, 2-methyl-4-amino-(N-tetrahydrofurfuryl)-aniline, 2-chloro-4-amino-(N-tetrahydrofurfuryl)-aniline, 2-methyl-4-amino-(N-furfuryl)-aniline, N,N-bis-(β-hydroxyethyl)-para-phenylenediamine, 4-amino-N-ethyl-N-(β-mesylaminoethyl)-aniline, 4-amino-N-ethyl-N-(α-carbamylmethyl)-aniline, 4-amino-N-ethyl-N-(β-piperidinoethyl)-aniline, N-(β-hydroxyethyl)-N-(β-mesylaminoethyl)-p-phenylenediamine, N-(4'-aminophenyl)-piperidine, N-(4'-aminophenyl)-morpholine, 3-methyl- 4-amino-N-ethyl-N-(α-carbamylmethyl)-aniline, 3-methyl-4-amino-N-ethyl-N-(β-mesylaminoethyl)-aniline, 3-chloro-4-amino-N,N-bis-(β-hydroxylethyl)-aniline, 3-methyl-4-amino-N,N-dimethylaniline, 3-chloro-4-amino-N,N-dimethylaniline, 3-methoxy-4-amino-N,N-dimethylaniline, N,N'-(β-hydroxyethyl)-N,N'-(4-aminophenyl)-tetramethylenediamine and N,N'-(β-hydroxyethyl)-N,N'-(4-aminophenyl)-dimethylenediamine, as well as the organic or inorganic acid salts of these bases, such as the hydrochloride, hydrobromide, sulphate, methosulphate, acetate and tartrate.

Amongst the precursors of the ortho type which give particularly significant results, there may be mentioned ortho-phenylenediamine, ortho-aminophenol, and N-substituted derivatives thereof, such as 2-N-(β-hydroxyethyl)-aminophenol and 4-methoxy-2-amino-N-(β-hydroxyethyl)-aniline, and ortho-diphenol.

The molar proportions of the oxidative dyestuff precursors of the para type, relative to the oxidative dyestuff precursors of the ortho type, is generally from 30:1 and 0.5:1 and preferably 20:1 to 1:1.

Other para oxidative bases can be added to the mixture of the para oxidative dyestuff precursors and ortho compounds as defined above; these bases include: para-phenylenediamines, such as para-phenylenediamine, para-toluylenediamine, methoxy-para-phenylenediamine, chloro-para-phenylenediamine, N,N-dimethyl-para-phenylenediamine and para-aminodiphenylamine, and para-aminophenols, such as para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol and N-methyl-para-aminophenol.

It is also possible to add, to the mixture of the para bases and ortho compounds defined above, one or more diphenylamines, in particular the diphenylamines in which the 2 benzene nuclei are substituted in the 4- and 4'-position by 2 groups such as hydroxyl and/or

in which R' and R" independently (or simultaneously) denote: hydrogen, alkyl or hydroxyalkyl, R" can denote carbamylalkyl, mesylaminoalkyl, acetylaminoalkyl, sulphoalkyl, piperidinoalkyl, morpholinoalkyl or benzoylaminoalkyl, and R' denotes H or alkyl. The radicals R' and R" can form, together with the nitrogen atom to which they are attached, a piperidino or morpholino heterocyclic ring. The other positions of the benzene nuclei can be occupied by one or more groups, such as alkyl or alkoxy, a halogen atom or a ureido or amino group which is optionally substituted by a hydroxyalkyl, carbamylalkyl, mesylaminoalkyl, acyl or carbalkoxy group or an alkylene group forming a heterocyclic ring together with a primary or secondary amine group in the 4- or 4'-position.

These diphenylamines can be used in the form of their salts such as the sulphate, hydrobromide, hydrochloride, acetate or tartrate.

These diphenylamines are described in, for example, French Patents Nos. 1,222,700, 2,056,799, 2,174,473, 2,145,724, 2,262,023, 2,262,024 and 2,261,750 and Patent Application No. 75/05,503.

Examples which may be mentioned are: 3,5-dimethyl-4-hydroxy-4'-N,N-dimethylaminodiphenylamine, 2-acetylamino-2',3,5-trimethyl-4-hydroxy-4'-N-ethyl-N-(β-mesylaminoethyl)-aminodiphenylamine, 2-acetylamino-2',5-dimethyl-4-hydroxy-4'-N-ethyl-N-carbamylmethyl-aminodiphenylamine, 2',3,5,5'-tetramethyl-4-hydroxy-4'-aminodiphenylamine, 2,4-diamino-3-methoxy-4'-hydroxydiphenylamine dihydrochloride, 3,5-dimethyl-4-hydroxy-4'-aminodiphenylamine, 2-carbamylmethyl-amino-4-hydroxy-4'-N,N-di-(β-hydroxyethyl)-amino-5-methyldiphenylamine, 3,5-dimethyl-4,4'-dihydroxydiphenylamine, 2'-chloro-3,5-dimethyl-4,4'-dihydroxydiphenylamine hydrochloride, 2,4'-diamino-4-hydroxy-5-methyldiphenylamine, 2-hydroxyethylamino-5-methyl-4,4'-dihydroxydiphenylamine and 2-amino-5-methyl-4,4'-dihydroxydiphenylamine.

The composition according to the invention can contain a mercaptan corresponding, for example, to the formula:

$$R-SH \qquad (II)$$

in which R denotes an alkylene group bonded to a group —COOH, —CONH$_2$, —OH, —SH or —COOR', R' denoting an alkyl group which is unsubstituted or substituted by one or more OH groups, it being possible for the said alkylene group to be substituted by one or more lower alkyl, amino or COOH groups, as well as the ammonium, alkali metal and alkaline earth metal salts of these compounds and the salts derived from organic and inorganic acids.

In formula II, the alkylene group preferably has 1 to 4 carbon atoms and denotes, in particular, a methylene, ethylene or propylene group; the alkyl group preferably denotes a group having 1 to 4 carbon atoms and, in particular, a methyl group; the alkali metal or alkaline earth metal salts are preferably sodium, potassium or calcium salts; the salts of organic or inorganic acids are preferably salts derived from hydrochloric, sulphuric, acetic or tartaric acid.

Amongst the abovementioned compounds of the formula (II), the preferred compounds are, inter alia, thioglycollic acid, thiolactic acid, β-mercaptopropionic acid, thioglycerol, glycerol thioglycollate, thioglycol, glycol thioglycollate, thioglycolamide, cysteine hydrochloride, mercaptosuccinic acid and α,α'-dimercaptoadipic acid.

These mercaptans can be used singly or in a mixture.

These mercaptans are preferably present in amounts of less than 5% by weight so as not to degrade the hair.

A particularly advantageous embodiment of the invention consists of a composition of the above-mentioned type, in which the mercaptan is present in an amount from 1 to 5% by weight and in particular from 1.5 to 3.5% by weight. Such compositions make it possible, in particular, to overcome the selectivity problems presented by some of the said oxidative bases.

According to a preferred embodiment of the invention, the oxidative dyestuff precursors of the para and ortho type are present in amounts from about 0.005% to 10% by weight and preferably from 0.01% to 8% by weight.

The pH of the composition according to the invention is suitably from 7 to 12 and preferably from 8.5 to 11.

It can be adjusted by means of cosmetically acceptable alkalising agents such as ammonia, alkylamines, alkanolamines, such as mono-, di- or tri-ethanolamine, alkylalkanolamines, such as aminomethylpropanol and aminomethylpropanediol, sodium hydroxide or potassium hydroxide and sodium carbonate or potassium carbonate or a mixture thereof.

This composition can, inter alia, be buffered to a defined pH by means of inorganic or organic salts such neutral or acid phosphates or ammonium, alkali metal or alkaline earth metal carbonates.

The compositions according to the invention can be applied directly to the hair, in accordance with the conventional dyeing processes, after mixing them with a cosmetically acceptable oxidising agent such as hydrogen peroxide.

According to a particularly advantageous embodiment, these compositions are used in a two-stage process which consists, in a first stage, in applying the composition defined above to the fibres for a sufficient length of time to impregnate the latter, and, in a second stage and without intermediate rinsing in applying a composition containing an oxidising agent which is present in a sufficient amount to develop the dye of the hair.

If desired, it is possible, in a third stage and before the oxidising agent has caused the complete development of the para oxidative dyestuff precursors and ortho oxidative dyestuff precursors present on the hair, to apply, without intermediate rinsing, a composition containing couplers, and in particular so-called meta compounds, this makes it possible to vary the shade of the resulting colour by combination with the said para bases and the ortho compounds.

Finally, it is possible to apply the said composition to the hair after mixing it with an oxidising agent, and then, before the oxidising agent has completely developed the dyestuffs and without intermediate rinsing, to apply a composition containing the coupler.

In fact, we have discovered that, by applying this process, the strength of the resulting coloration is substantially greater than that obtained when using a single composition consisting of the coupler and the combination of a para and ortho oxidative dyestuff precursor. This difference seems to be due to the fact that, when it is present in the mixture of para base and ortho compound, the coupler tends to react more rapidly with the bases with the result that this coupling takes place in preference to the condensation of the ortho compound with the para base.

Amongst the couplers which can more particularly be used according to the invention, there may be mentioned: monophenol derivatives, meta-diphenols, meta-aminophenols having a free primary, secondary or tertiary amin group or a blocked (substituted) amino group, and meta-diamines. These various classes can be represented by the general formula:

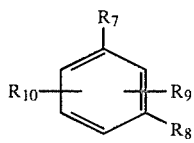
(III)

in which:

if formula III represents a phenol coupler, only one of the substituents $R_7$ or $R_8$ denotes OH and the other substituents, which are different from OH, denote hydrogen, alkyl, alkoxy or halogen, one of the para or ortho positions relative to the OH group being free or substituted by halogen or alkoxy;

if formula III represents a m-diphenol, $R_7$ and $R_8$ denote OH, it being possible for $R_9$ and $R_{10}$ to denote hydrogen, an alkyl or alkoxy group or halogen;

if formula III represents a m-aminophenol, one of the groups $R_7$ or $R_8$ denotes OH and the other group represents

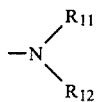

in which: $R_{11}$ and $R_{12}$, which are identical or different, denote hydrogen, linear or branched alkyl optionally chain-terminated by a OH, alkoxy or optionally monosubstituted or disubstituted amino group, including a heterocyclic ring such as piperidino or morpholino, it being possible for the alkyl group to contain chain ether groups in the chain and/or be substituted by hydroxy or amino groups; or one of $R_{11}$ or $R_{12}$ denotes acyl, carbamyl, carbamylalkyl in which the nitrogen atom is unsubstituted or monosubstituted or disubstituted, alkyl- or arylsulphonyl, sulphonamidoalkyl in which the nitrogen atom is unsubstituted or monosubstituted or disubstituted, carbethoxy or mesylaminoalkyl, and the other denotes hydrogen; and $R_9$ and $R_{10}$, which are identical or different, denote hydrogen, halogen, linear or branched alkyl or a group $OZ_1$, $Z_1$ representing alkyl or forms a morpholino ring together with the nitrogen atom of $R_7$ or $R_8$; and if formula III denotes a m-diamine, $R_7$ and $R_8$ both denote a group

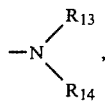

in which each $R_{13}$ and each $R_{14}$ independently, which are identical or different, denote hydrogen or a linear or branched alkyl which is optionally substituted by OH, amino, alkoxy, carbamyl or alkyl- or aryl-sulphonylamino, or one of $R_{13}$ and $R_{14}$ denotes an alkylsulphonyl, acyl or carbamylalkyl group and the other denotes hydrogen; and $R_9$ and $R_{10}$, which are identical or different, denote hydrogen, halogen, linear or branched alkyl or $OZ_2$, $Z_2$ denoting alkyl, hydroxyalkyl, alkoxyalkyl, arylaminoalkyl, mesylaminoalkyl, ureidoalkyl or carbalkoxyalkyl; or forming with the nitrogen atom of $R_7$ or $R_8$ a morpholino ring and also the organic or inorganic acid salts thereof such as the hydrochloride, hydrobromide, sulphate, acetate and tartrate.

In the formulae of the abovementioned couplers, the alkyl group preferably denotes a group from 1 to 6 carbon atoms, such as a methyl, ethyl, propyl, isopropyl, n-butyl or i-butyl group, alkoxy denotes a group preferably having 1 to 6 carbon atoms, such as methoxy, ethoxy or propoxy, halogen denotes chlorine, bromine or fluorine, and the substituents on the nitrogen atom are preferably alkyl groups having from 1 to 6 carbon atoms.

Amongst the couplers corresponding to the general formula mentioned above, the following may be singled out more particularly: resorcinol, 2-methylresorcinol, 4-chlororesorcinol, meta-aminophenol, 2,4-diaminoanisole, 2-methyl-5-ureidophenol, 2,6-dimethyl-3-aminophenol, 2-methyl-5-acetylaminophenol, 2,6-dimethyl-5-acetylaminophenol, 3-amino-4-methoxyphenol, 2-methyl-5-N-(β-hydroxyethyl)-aminophenol, meta-phenylenediamine, meta-toluylenediamine, N-methyl-meta-aminophenol, 6-methyl-3-aminophenol, 2,4-diaminophenoxyethanol, 3-N,N-diethylaminophenol. 6-methyl-3-N-(β-mesylaminoethyl)-aminophenol, 6-methyl-3-N-(carbamylmethylaminophenol, 3-N-carbamylmethylaminophenol, 2-N-(β-hydroxyethyl)-amino-4-aminophenoxyethanol and 3-N,N-diethylaminophenol and the salts of these compounds.

Other couplers which can be used in the compositions according to the invention include, naphthols, heterocyclic compounds, such as morpholine derivatives, for example 6-hydroxybenzomorpholine and 6-aminobenzomorpholine, pyridine derivatives, such as 2,6-diaminopyridine, and diketone compounds and their salts.

According to a preferred embodiment of the invention, the couplers are present in amounts from about 0.005% to 10% by weight and preferably from 0.01 to 8% by weight.

The two-stage process mentioned above can also be carried out advantageously by using, as the first composition, the composition of the present invention which additionally contains at least one mercaptan in the proportions indicated above.

In the two-stage process, the application time of the first composition is generally 5 to 45 minutes, and preferably 5 to 20 minutes, whereas the time of action of the oxidising composition is generally 5 to 45 minutes, preferably 10 to 40 minutes, the time of action of the possible third composition containing the coupler being generally 5 to 45 minutes and preferably 10 to 30 minutes.

In this process, it is possible, by varying the application time and the amount of oxidising agent, to dye the hair so as to lighten the colour to a greater or lesser degree. It is also possible to vary the strength of the coloration by varying the amount of mercaptan within the range defined above, it being possible for the mercaptan to be added in the abovementioned amounts, just before use, to the compositions in which the oxidisable dyestuff is present.

The mercaptan can also be applied directly to the hair before application of the compositions intended for dyeing the hair.

Again it is possible, in a first stage, to apply a first composition containing the mercaptan in the proportions defined above, and, in a second stage and without previous rinsing, a second composition containing the oxidising agent and also containing the para and ortho oxidative dyestuff precursors for dyeing the hair, and, optionally, to applying one or more couplers in a further stage.

The oxidising composition applied in the second stage contains a cosmetically acceptable oxidising agent such as hydrogen peroxide, suitably at a concentration of 0.1 to 20% by weight, urea peroxide or a persalt such as ammonium persulphate, sodium persulphate or potassium persulphate. The pH of this composition can be adjusted so as to give optimum development of the coloration, after penetration into the fibre, of this composition and the composition applied in the first stage.

The compositions according to the invention which contain at least one para oxidative dyestuff precursor of the abovementioned type and one oxidative dyestuff precursor of the ortho type, and also the oxidising compositions or the compositions containing couplers which can be used in the multi-stage dyeing process, can also be used with direct dyestuffs or hydroxynaphthoquinones, which can be present in the composition according to the invention, if they are stable in the latter, or in the compositions applied in the second stage, if they are stable in an oxidising medium, or also in the composition containing the coupler. The process according to the invention thus makes it possible not only to utilise, to the maximum extent, the colouring potentials of the various abovementioned oxidative dyestuff precursors of the para and ortho type, but also to combine the action of these dyestuff precursors with that of direct dyestuffs which could not previously be used under the normal conditions of use of oxidative dyes.

The direct dyestuffs and the hydroxynaphthoquinones are preferably present in amounts from about 0.005% to 3% by weight.

The direct dyestuffs which can more particularly be used in the process according to the invention are anthraquinone dyestuffs, nitro benzene series and nitrated diphenylamines, in particular nitrophenylenediamines, nitroaminophenols, dinitroaminophenols, dinitroaminobenzenes, nitroaminobenzenes and nitrodiphenylamines such as those described in French Pat. No. 2,211,210. There may be mentioned, in particular: 1-hydroxy-2-amino-4,6-dinitrobenzene, 2-nitro-p-phenylenediamine, 1-amino-2-nitro-4-N-methylaminobenzene, 1-hydroxy-2-amino-5-nitrobenzene, 4-nitro-m-phenylenediamine, 1-methoxy-3-nitro-4-N-($\beta$-hydroxyethyl)-aminobenzene, 1-($\beta$-hydroxyethoxy)-3-nitro-4-aminobenzene, 2-N-($\beta$-hydroxyethyl)-amino-5-nitroanisole, 1-amino-2-nitro-4-N-($\beta$-hydroxyethyl)-aminobenzene, 1-N-methylamino-2-nitro-4-N,N-bis-($\beta$-hydroxyethyl)-aminobenzene, 1-N-methylamino-2-nitro-4-N-methyl-N-($\beta$-hydroxyethyl)-aminobenzene, 3-nitro-4-N-($\beta$-hydroxyethyl)-aminophenol, 2,6-dimethyl-3-nitro-4-N-($\beta$-hydroxyethyl)-aminophenol, 4-nitro-o-phenylenediamine, 2-amino-4-nitrophenol, 2-nitro-4-aminophenol, 1,4-N,N-bis-($\beta$-hydroxyethyl)-amino-2-nitrobenzene, 1-amino-2-N-($\beta$-hydroxyethyl)-amino-5-nitrobenzene, 3-nitro-4-N'-($\beta$-hydroxyethyl)-amino-N,N-bis-($\beta$-hydroxyethyl)-aniline, 2-N-($\beta$-hydroxyethyl)-amino-5-nitrophenoxyethanol, 1-amino-2-[tris-(hydroxymethyl)-methyl]-amino-5-nitrobenzene, 1-N-($\beta$-hydroxyethyl)-amino-2-nitrobenzene, 2-nitro-4-N'-($\beta$-hydroxyethyl)-amino-N,N-bis-($\beta$-hydroxyethyl)-aniline, 2-nitro-4'-bis-($\beta$-hydroxyethyl)-aminodiphenylmine, 2-nitro-4'-hydroxydiphenylamine, 1-amino-3-nitro-4-N-($\beta$-hydroxyethyl)-aminobenzene, 2-N,N-bis-($\beta$-hydroxyethyl)-amino-5-nitrophenol, 1-amino-2-nitro-4-N-($\beta$-hydroxyethyl)-amino-5-chlorobenzene, 3-nitro-4-aminophenol, 5-amino-2-nitrophenol, 2-nitro-4-aminodiphenylamine, 3-nitro-4-N'-($\beta$-hydroxyethyl)-amino-N-methyl-N-($\beta$-hydroxyethyl)-aniline and 3-nitro-4-N'-($\beta$-hydroxyethyl)-amino-N-methylaniline.

The hydroxynaphthoquinones which are particularly preferred are 2-hydroxy-1,4-naphthoquinone and 5-hydroxy-1,4-naphthoquinone.

These various compositions which can be used according to the invention can be in the form of, for example, aqueous, thickened, gelled or gellable compositions or in the form of creams or an aerosol.

The gelled or gellable compositions are typically obtained either from polyoxyethleneated or polyglycerolated non-ionic compounds in the presence of solvents, or from soaps of liquid fatty acids, such as oleic acid or isostearic acid, in the presence of solvents in an aqueous vehicle.

The fatty acids are generally used to form the soaps at concentrations from 0.5 to 15% by weight.

The alkalising agents used to form the soaps can be, in particular, sodium hydroxide, potassium hydroxide, ammonia, monoethanolamine, diethanolamine, triethanolamine or mixtures thereof.

Amongst the polyoxyethyleneated non-ionic compounds, there may be mentioned, in particular, polyoxyethyleneated nonylphenol containing 4 mols of ethylene oxide (per mole of phenol) and polyoxyethyleneated nonylphenol containing 9 mols of ethylene oxide.

These constituents are preferably present at concentrations from 5 to 60% by weight.

Amongst the polyglycerolated non-ionic compounds, there may be mentioned, in particular, polyglycerolated oleyl alcohol containing 2 mols of glycerol and polyglycerolated oleyl alcohol containing 4 mols of glycerol.

These constituents are preferably present at concentrations from 5 to 60% by weight.

Amongst the solvents which can be used, there may be mentioned ethyl, isopropyl and butyl alcohols, glycols or glycol ethers, such as methylcellosolve, ethylcellosolve, butylcellosolve (ethylene glycol monomethyl, monoethyl and monobutyl (ether) propylene glycol, carbitol and butylcarbitol, and benzyl alcohol.

These constituents are preferably present at concentrations from 2 to 40% by weight.

All the concentrations are indicated relative to the total weight of the dyeing composition.

If the compositions are in the form of creams, their formulation is essentially based on soaps or fatty alcohols, in the presence of emulsifying agents and in an aqueous vehicle.

The soaps can be formed from natural or synthetic fatty acids having from 12 to 18 carbon atoms, such as lauric acid, myristic acid, palmitic acid and stearic acid, and from alkalising agents such as sodium hydroxide, potassium hydroxide, ammonia, monoethanolamine, diethanolamine and triethanolamine. The fatty acids are preferably present in the creams of the invention at concentrations from 10 to 30% by weight.

The creams can also be formulated from natural or synthetic fatty alcohols having 12 to 18 carbon atoms, in a mixture with emulsifying agents. Amongst these fatty alcohols, there may be mentioned, in particular, lauryl alcohol, alcohols derived from copra fatty acids, myristyl alcohol, cetyl alcohol, stearyl alcohol and hydroxystearyl alcohol. The concentrations of fatty alcohols in the creams of the invention is generally 5 to 25% by weight.

The emulsifying agents which can be used in the compositions according to the present invention include polyoxyethyleneated or polyglycerolated fatty alcohols such as polyoxyethyleneated oleyl alcohol containing from 10 to 30 mols of ethylene oxide, polyoxyethyleneated cetyl alcohol containing from 6 to 10 mols of ethylene oxide, polyoxyethyleneated lauryl alcohol containing 12 mols of ethylene oxide, oxyethyleneated cetyl/stearyl alcohol containing 10 or 15 mols of ethylene oxide, polyoxyethyleneated oleyl/cetyl alcohol containing 30 mols of ethylene oxide, polyoxyethyleneated stearyl alcohol containing 10, 15 or 20 mols of ethylene oxide, polyglycerolated oleyl alcohol containing 4 mols of glycerol and synthetic fatty alcohols which contain 9 to 15 carbon atoms and are polyoxyethyleneated with 5 or 10 mols of ethylene oxide; polyoxyethyleneated castor oil can also be used. These non-ionic emulsifying agents are present in the compositions of the invention in amounts of, say, 1 to 25% by weight.

Other emulsifying agents which can be used according to the invention are alkyl-sulphates which may or may not be oxyethyleneated, such as sodium lauryl-sulphate, ammonium lauryl-sulphate, sodium cetyl-/stearyl-sulphate, triethanolamine cetyl-/stearyl-sulphate, monoethanolamine lauryl-sulphate or triethanolamine lauryl-sulphate, the sodium salt of the sulphate half-ester of oxyethyleneated lauryl alcohol containing, for example, 2.2 mols of ethylene oxide and the monoethanolamine salt of the sulphate half-ester of oxyethyleneated lauryl alcohol containing, for example, 2.2 mols of ethylene oxide.

These constituents are preferably present in the compositions of the invention at concentrations from 1 to 15% by weight.

In addition to soaps, fatty alcohols and emulsifying agents, the creams according to the invention can contain adjuvants, such as fatty amides, which are usually employed in such compositions.

Amongst the fatty amides, mono- or di-ethanolamides of acids derived from copra, of lauric acid or of oleic acid are preferably used, at concentrations up to 10% by weight, relative to the total weight of the composition.

An antioxidant, intended to avoid changes in the dyeing capacity, can advantageously be added.

Examples which may be mentioned are sodium sulphite, sodium bisulphite and sodium dithionite and ascorbic acid or isoascorbic acid and their esters and their salts. The concentrations of these compounds is suitably up to 1%.

The compositions according to the invention can also contain solvents, thickeners, treating agents, sequestering agents, such as ethylenediaminetetraacetic acid, diethylenetriaminepentaacetic acid or their salts, perfumes, preservatives and sun filters, for example.

Solvents can be added to the composition in order to solubilise the dyestuffs which are insufficiently soluble in water. In this case, the solvents which can be used may be the same as those indicated above for the composition of the gellable liquids.

Amongst the thickeners which can be used according to the invention, there may be mentioned sodium alginate or gum arabic, cellulose derivatives, such as methylcellulose, hydroxyethylcellulose, hydroxypropylcellulose, hydroxypropylmethylcellulose and carboxymethylcellulose, or carboxyvinylic polymers such as the carbopols.

These constituents are suitably present in amounts of 0.5 to 5%.

The treating agents which can be used according to the invention are mainly intended to improve the feel of the hair and to make the hair easier to comb out. They can be, for example, cationic polymers such as quaternary derivatives of cellulose ether, for example JR 400 of Union Carbide, polydiallyldimethylammonium chlorides, for example Merquat 550 and Merquat 100 of Merck, the quaternised polymers as defined in French Pat. Nos. 2,270,846, 2,316,271, 2,189,434 and 75/15,161 of the Applicant Company, and the cross-linked, cationic graft copolymers described in French Pat. No. 73/22,222 used singly or in a mixture; the concentration of treating agent is suitably from 0.1 to 5% by weight.

The two-stage process according to the invention also makes it possible to vary the consistency and the form of the dyeing carrier between the time of application of the compositions to the hair and the dyeing itself. It is thus possible, in an advantageous embodiment of the invention, to apply the first composition to the hair in the form of a liquid, which assists the impregnation of the hair, and the second composition containing ingredients which react with the first composition on the hair, modifying its consistency, for example by gelling, which facilitates the application of the dye to the hair.

The so-called "trinuclear" compounds which constitute a further subject of the invention are represented by the general formula:

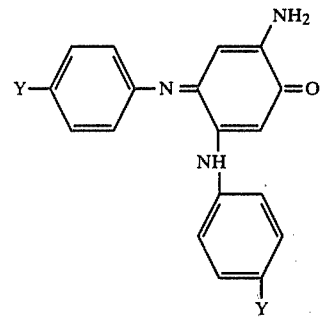

in which Y represents

$R'_1$ and $R'_2$ independently of one another denoting alkyl, mesylaminoalkyl, piperidinoalkyl or hydroxyalkyl group, the alkyl groups containing 1 to 6 carbon atoms, and their cosmetically acceptable salts.

These compounds can be prepared by reacting about 1 mol of the corresponding aminoaniline with 1 mol of orthoaminophenol in an oxidising alkaline medium.

The following Examples further illustrate the present invention; Examples A and B illustrate the preparation of compounds to be used in the present invention.

EXAMPLE A

Preparation of the
N-(β-hydroxyethyl)-N-(β-mesylaminoethyl)-para-phenylenediamine dihydrochlorine monohydrate used in composition S₁₃

Preparation of
4-acetylamino-N-(β-mesylaminoethyl)-aniline 0.2 mol (25.2 g) of sodium sulphite is added, at ambient temperature, to a solution of 0.1 mol (32.7 g) of N-(β-mesylaminoethyl)-para-phenylenediamine sulphate in 150 ml of water, and 0.13 mol (13.17 g) of acetic anhydride is added gradually, whilst stirring. When the addition is complete, stirring is continued for one hour and the expected acetylated derivative which has precipitated in crystalline form is then filtered off. The product is drained, washed with water and dried in vacuo. After recrystallisation from alcohol and drying in vacuo, it melts at 130° C.

| Analysis | Calculated for $C_{11}H_{17}N_3SO_3$ | Found |
|---|---|---|
| C% | 48.71 | 48.71 |
| H% | 6.27 | 6.15 |
| N% | 15.50 | 15.80 |
| S% | 11.81 | 12.01 |

Preparation of
4-acetylamino-N-(β-hydroxyethyl)-N-(β-mesylaminoethyl)-aniline 0.037 mol (10 g) of 4-acetylamino-N-(β-mesylaminoethyl)-aniline is dissolved in 31 ml of boiling water. 7.4 g of sodium carbonate and 0.148 mol (18.5 g) of glycol bromohydrin are added, whilst stirring. After stirring for 4 hours in a boiling water bath, the reaction medium is filtered and the filtrate is then left to stand for 48 hours at 0° C. The 4-acetylamino-N-(β-hydroxyethyl)-N-(β-mesylaminoethyl)-aniline which has precipitated in crystalline form is filtered off. After recrystallisation from boiling water and drying in vacuo, the products melts at 118° C.

| Analysis | Calculated for $C_{13}H_{21}N_3SO_4$ | Found |
|---|---|---|
| C% | 49.52 | 49.80 |
| H% | 6.67 | 6.77 |
| N% | 13.33 | 13.16 |
| S% | 10.16 | 10.36 |

Preparation of
N-(β-hydroxyethyl)-N-(β-mesylaminoethyl)-para-phenylenediamine dihydrochloride monohydrate 0.0178 mol (5.6 g) of 4-acetylamino-N-(β-hydroxyethyl)-N-(β-mesylaminoethyl)-aniline in 12 ml of a 5 N aqueous solution of hydrochloric acid is heated for 30 minutes in a boiling water bath. The water is then driven off in vacuo. After keeping the residue for two hours in vacuo at 60° C., a crystalline product, which is chromatographically pure, is obtained.

Molecular weight calculated for

| $C_{11}H_{19}N_3O_3S \cdot 2HCl \cdot H_2O$ | 366 |
|---|---|
| Molecular weight obtained by potentiometric determination | 358 |

| Analysis | Calculated for $C_{11}H_{19}N_3O_3S \cdot 2HCl \cdot H_2O$ | Found | |
|---|---|---|---|
| C% | 36.26 | 35.97 | 36.08 |
| H% | 6.31 | 6.40 | 6.44 |
| N% | 11.53 | 11.39 | 11.28 |
| Cl% | 19.50 | 19.54 | 19.66 |

EXAMPLE B

Preparation of
4-N-[β-(β'-hydroxyethoxy)-ethyl]-aminoaniline sulphate

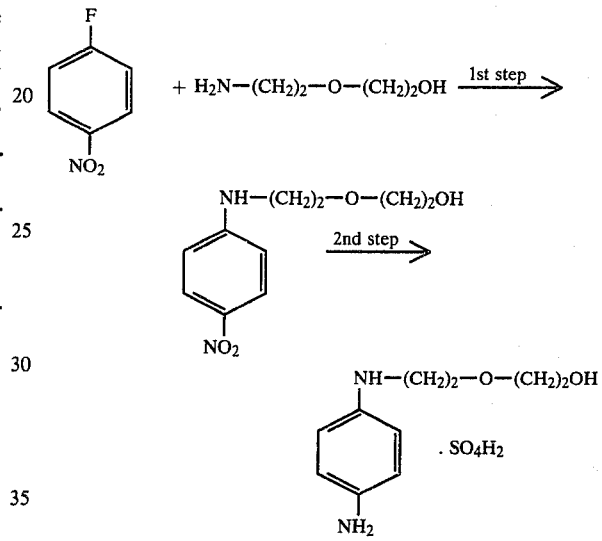

1st step: Preparation of 4-nitro-N-[β-(β'-hydroxyethoxy)-ethyl]-aniline.

0.2 mol (28.2 g) of para-fluoronitrobenzene in 84.6 ml of diglycolamine is heated for 2 and a half hours at between 110° and 120° C. After cooling the mixture, it is poured onto 300 g of crushed ice. The expected product precipitates in crystalline form. It is filtered off, washed with water and dried. After recrystallisation from ethanol and drying in vacuo, it melts at 78° C. Elementary analysis of the product obtained gives the following results:

| Analysis | Calculated for $C_{10}H_{14}O_4N_2$ | Found |
|---|---|---|
| C% | 53.09 | 53.20 |
| H% | 6.19 | 6.32 |
| N% | 12.39 | 12.32 |

2nd stage: Preparation of 4-N-[β-(β'-hydroxyethoxy)-ethyl]-aminoaniline sulphate.

7.5 g of ammonium chloride and 58.5 g of zinc powder are added to 175 ml of an aqueous-ethanolic solution (15% of water, 85% of ethanol). This mixture is heated to the reflux temperature, whilst stirring, and 0.15 mol (33.9 g) of the product obtained in the first step is then added in small portions. When the addition of the nitro derivative is complete, the reaction medium is decolourised; it is filtered at the boil, the filtrate being collected in a flask, cooled to −10° C., containing 10.5 ml of concentrated sulphuric acid and 30 ml of ethanol. The expected product precipitates in the form of a gum which crystallises rapidly. The crystals are filtered off and washed with alcohol and then acetone. After drying in vacuo, the product melts at about 157° C. with decomposition. After recrystallisation from an aqueous-ethanolic mixture, the product obtained is subjected to elementary analysis which gives the following results:

| Analysis | Calculated for $C_{10}H_{18}N_2O_6S$ | Found |
|---|---|---|
| C% | 40.82 | 40.65 |
| H% | 6.12 | 6.07 |
| N% | 9.52 | 9.53 |
| S% | 10.88 | 10.92–10.69 |

EXAMPLE C

Compound, with three aromatic nuclei, of the formula:

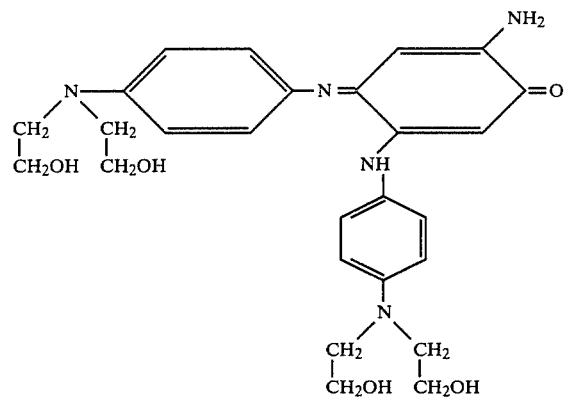

0.022 mol (6.5 g) of 4-N,N-bis-(β-hydroxyethyl)-aminoaniline sulphate and 0.023 mol (2.6 g) of orthoaminophenol are dissolved in 200 ml of an aqueous-ethanolic solution (40% of ethanol, 60% of water).

40 ml of 22° B strength ammonia solution and 100 ml of hydrogen peroxide of 20 volumes strength are added. After stirring for two hours at ambient temperature, the expected product is filtered off. After recrystallisation from methanol and drying in vacuo, the product melts at 170° C.

Molecular weight calculated for $C_{26}H_{33}N_5O_5$: 495. Molecular weight found by potentiometric determination in acetic acid using a perchloric acid solution: 503 (for 3 titratable groups).

Its structure was proved by an NMR study.

Molecular weight: 495 from the mass spectrum.

| Analysis | Calculated for $C_{26}H_{33}N_5O_5$ | Found |
|---|---|---|
| C% | 63.03 | 62.73 |
| H% | 6.66 | 7.00 |
| N% | 14.14 | 13.90–14.12 |
| | | 17.04–17.10 |

EXAMPLE NO. 1

The following compositions are prepared:

Composition $S_1$:
2,6-Dimethyl-5-methoxy-para-phenylenediamine

| -continued | | |
|---|---|---|
| dihydrochloride | 2.40 | g |
| Ortho-aminophenol | 0.33 | g |
| Remcopal 334 | 22 | g |
| Remcopal 349 | 22 | g |
| Butylglycol | 8 | g |
| Propylene glycol | 8 | g |
| Crosslinked polyacrylic acid | 0.5 | g |
| Masquol DTPA | 2.5 | g |
| 35° Bé strength sodium bisulphite solution | 0.5 | cc |
| Ammonium thiolactate[x] | 1.5 | g |
| Monoethanolamine | 7 | cc |
| Water, q.s.p. | 100 | g |
| Composition $S_2$: | | |
| Polychol 5 | 3.3 | g |
| Polychol 20 | 1.7 | g |
| Cetyl/stearyl alcohol | 5 | g |
| Hydrogen peroxide of 100 volumes strength | 20 | g |
| Phosphoric acid q.s.p. | pH 3 | |
| Water, q.s.p. | 100 | g |

[x]The ammonium thiolactate is added at the time of use.

40 g of the composition $S_1$ are applied for 10 minutes to a very light blond head of hair containing a high percentage of white hair.

40 g of the composition $S_2$ are then applied without rinsing. The gel thus obtained is left on the hair for 20 minutes and the head of hair is then rinsed, shampooed and dried; it is coloured dull deep blond.

If, on the other hand, an identical composition containing only one of the two dyestuffs at an equivalent concentration ($1.3 \times 10^{-2}$ mol %) is applied in the same manner, only an ashen very light blond shade is achieved with the above para-phenylenediamine and only a golden deep blond shade is achieved with ortho-aminophenol, these shades being less resistant to several shampooings than the dye obtained with the mixture of these two oxidative dyestuff precursors.

EXAMPLE NO. 2

The following composition is prepared:

| Composition $S_3$: | | |
|---|---|---|
| 4-Amino-N-ethyl-N-(α-carbamylmethyl)-aniline | 1.93 | g |
| Ortho-aminophenol | 0.33 | g |
| Remcopal 334 | 21 | g |
| Remcopal 349 | 24 | g |
| Oleic acid | 4 | g |
| Butylglycol | 3 | g |
| Absolute ethyl alcohol | 14 | g |
| Masquol DTPA | 2.5 | g |
| 35° Bé strength sodium bisulphite solution | 0.5 | cc |
| Glycerol monothioglycollate | 2.5 | g |
| Sodium bicarbonate | 0.35 | g |
| Sodium hydroxide | 0.07 | g |
| 22° Bé strength ammonia solution | 8 | cc |
| Water, q.s.p. | 100 | g |

The glycerol monothioglycollate is added at the time of use.

30 g of the creamy composition $S_3$ are applied for 7 minutes to a light chestnut head of hair having a low percentage of white hair.

30 g of the following composition $S_4$:

| Composition $S_4$: | | |
|---|---|---|
| Polychol 5 | 3.3 | g |
| Polychol 20 | 1.7 | g |
| Cetyl/stearyl alcohol | 5 | g |
| Hydrogen peroxide of 100 volumes strength | 30 | g |
| Phosphoric acid q.s.p. | pH 3 | |

| | | |
|---|---|---|
| -continued | | |
| Water q.s.p. | 100 | g | are then applied without rinsing.

The head of hair is massaged thoroughly and the mixture is left on the hair for about a further 20 minutes. After rinsing with warm water, shampooing and drying, the hair is uniformly coloured deep chestnut, whereas, if an identical composition containing only one of these components at a concentration of $1.3 \times 10^{-2}$ mol % is applied in the same manner, the same head of hair is coloured ashen deep blond with the above para-phenylenediamine and golden deep blond with ortho-aminophenol. Furthermore, the deep chestnut shade obtained by combining these two para and ortho compounds exhibits an enhanced resistance with respect to several shampooings.

EXAMPLE NO. 3

The following dyeing composition is prepared:

| Composition $S_5$: | | |
|---|---|---|
| N,N-bis-($\beta$-Hydroxyethyl)-para-phenylenediamine sulphate monohydrate | 1.60 | g |
| Ortho-aminophenol | 0.82 | g |
| Alfol C 16/18 E | 8 | g |
| Lanette wax E | 0.5 | g |
| Cemulsol B | 1 | g |
| Oleyl diethanolamide | 1.5 | g |
| Ethylenediaminetetraacetic acid | 0.3 | g |
| Ammonium thiolactate | 1.25 | g |
| 22° Bé strength ammonia solution | 12 | cc |
| Water q.s.p. | 100 | g |

15 g of this creamy mixture are applied to the roots of a blond head of hair which has been permed 4 months previously. After 8 minutes, an additional 15 g of this cream are distributed over the whole of the head of hair and, after 2 minutes, 30 g of the composition $S_2$ are incorporated onto the entire head of hair and the mixture is left for about a further 30 minutes.

After rinsing, shampooing and drying, a very attractive dull, uniform deep chestnut shade is obtained which is more intense and substantially more resistant with respect to several shampooings than the shade obtained in the same manner with each of the oxidative dyestuff precursors, this shade being blond/light blond with the above N,N-bis-($\beta$-hydroxyethyl)-para-phenylenediamine by itself and golden deep blond with ortho-aminophenol.

EXAMPLE NO. 4

The following dyeing composition is prepared:

| | | |
|---|---|---|
| N-Ethyl-N-piperidinoethyl-para-phenylenediamine dihydrochloride | 3.2 | g |
| Ortho-aminophenol | 0.055 | g |
| Cetyl alcohol | 18 | g |
| 20% strength ammonium lauryl-sulphate solution | 12 | g |
| Cetyl/stearyl alcohol containing 15 mols of ethylene oxide | 3 | g |
| Lauryl alcohol | 5 | g |
| Masquol DTPA | 2.5 | g |
| Ammonium thioglycollate | 0.4 | g |
| 22° Bé strength ammonia solution | 11 | cc |
| Water q.s.p. | 100 | g |

7 g of this cream are mixed with 7 g of water before use. This creamy mixture is applied for 10 minutes to a 1 g swatch of demi-waved grey hair.

7 g of a 12% strength aqueous solution of hydrogen peroxide, adjusted to pH 3 with phosphoric acid, are then added and the mixture is then left on the hair for 20 minutes.

After rinsing and drying, the swatch is coloured beige grey, whereas, under the same conditions, the above para-phenylenediamine by itself hardly colours this type of fibre at all and ortho-aminophenol only enables a very pale yellow colour to be obtained.

EXAMPLE NO. 5

The following dyeing composition is prepared:

| Composition $S_6$: | | |
|---|---|---|
| N,N-bis-($\beta$-Hydroxyethyl)-para-phenylenediamine sulphate monohydrate | 0.94 | g |
| Ortho-phenylenediamine | 0.11 | g |
| Comperlan KD | 1.75 | g |
| Ethylene glycol distearate | 1 | g |
| Sodium lauryl-sulphate containing 2 mols of ethylene oxide | 12 | g |
| Blanose R 530 | 0.1 | g |
| Ethylenediaminetetraacetic acid | 0.2 | g |
| Thiolactic acid | 1 | g |
| 22° Bé strength ammonia solution | 10 | cc |
| Water q.s.p. | 100 | g |

40 g of this gel are applied to a light blond head of hair which is unevenly sensitised and contains a high percentage of white hair.

30 g of the composition $S_2$ are then added to the head of hair and, after 20 minutes, the hair is rinsed, shampooed and dried; it is coloured ashen grey, whereas, under the same conditions, the above para-phenylenediamine only enables a light blond tint to be obtained and orthophenylenediamine only enables a golden light blond shade to be obtained, these shades being substantially less resistant with respect to several shampooings than the shade obtained by mixing the two para and ortho compounds.

EXAMPLE NO. 6

The following compositions are prepared:

| Composition $S_7$: | |
|---|---|
| N-Ethyl-N-($\beta$-mesylaminoethyl)-para-phenylenediamine dihydrochloride | 3.30 g |
| Para-aminophenol | 0.54 g |
| Ortho-aminophenol | 0.54 g |
| Remcopal 334 | 21 g |
| Remcopal 349 | 24 g |
| Oleic acid | 3 g |
| Butylglycol | 3 g |
| Absolute ethyl alcohol | 14 g |
| Ethylenediaminetetraacetic acid | 0.2 g |
| Cysteine hydrochloride | 0.1 g |
| Thioglycollic acid | 1.7 g |
| 22° Bé strength ammonia solution | 12 cc |
| Water q.s.p. | 100 g |
| Composition $S_8$: | |
| Polychol 5 | 3.3 g |
| Polychol 20 | 1.7 g |
| Stearyl alcohol | 5 g |
| Hydrogen peroxide of 100 volumes strength | 60 g |
| Phosphoric acid q.s.p. | pH 3 |
| Water q.s.p. | 100 g |
| Composition $S_9$: | |
| Resorcinol | 0.44 g |
| Meta-aminophenol | 0.76 g |

| -continued | |
|---|---|
| Remcopal 334 | 20 g |
| Remcopal 349 | 20 g |
| Carbopol 934 | 1.25 g |
| Absolute ethyl alcohol | 8 g |
| Propylene glycol | 6 g |
| Ethylene glycol distearate | 0.5 g |
| Ethylenediaminetetraacetic acid | 0.2 g |
| 35° Bé strength sodium bisulphite solution | 0.5 cc |
| Citric acid q.s.p. | pH 6 |
| Water q.s.p. | 100 g |

30 g of the composition $S_7$ are applied for 10 minutes to hair which is coloured light chestnut.

15 g of the composition $S_8$ are then added, whilst thoroughly massaging the head of hair, and, after 5 minutes, 15 g of the composition $S_9$ are applied carefully and the mixture is left on the hair for 25 minutes.

After rinsing, shampooing and drying, the head of hair is uniformly coloured brown, whereas, under the same operating conditions, the mixture of the two "para" bases only enables a deep blond shade to be obtained and orthoaminophenol by itself only enables a golden deep blond tint to be obtained.

Furthermore, if the couplers in the composition $S_9$ are applied at the same time as the oxidative bases in the composition $S_7$, and if this composition is then applied in two stages without intermediate rinsing:
1st stage (10 minutes): 30 g of the composition $S_7$ + 15 g of he composition $S_9$
2nd stage (30 minutes): 15 g of the composition $S_8$, the same head of hair is only coloured dull chestnut after rinsing, shampooing and drying.

EXAMPLE NO. 7

The following dyeing composition is prepared:

| Composition $S_{10}$: | |
|---|---|
| N-Ethyl-N-($\beta$-mesylaminoethyl)-para-phenylene-diamine dihydrochloride | 3.30 g |
| Ortho-aminophenol | 0.33 g |
| 2-($\beta$-Aminoethyl)-aminoanthraquinone hydrochloride | 0.60 g |
| Remcopal 334 | 21 g |
| Remcopal 349 | 24 g |
| Oleic acid | 4 g |
| Butylglycol | 3 g |
| Absolute ethyl alcohol | 14 g |
| Masquol DTPA | 2.5 g |
| Mercaptosuccinic acid | 0.5 g |
| Ammonium thioglycollate | 3 g |
| 22° Bé strength ammonia solution | 10 cc |
| Water q.s.p. | 100 g |

40 g of this composition are applied to a light chestnut head of hair. After 12 minutes, 40 g of the composition $S_2$ are applied, whilst massaging the head of hair, and the mixture is left on the hair for a further 20 minutes.

After rinsing, shampooing and then drying, a deep chestnut shade is obtained, whereas, under identical conditions, the combination of the above para-phenylenediamine and the anthraquinone dyestuff only enables a golden deep blond shade to be obtained and ortho-aminophenol by itself only enables a golden blond shade to be obtained.

EXAMPLE NO. 8

The following dyeing compositions are prepared:

| Composition $S_{11}$: | |
|---|---|
| -continued | |
| N-Ethyl-N-($\beta$-mesylaminoethyl)-para-phenylene-diamine dihydrochloride | 3.30 g |
| Ortho-aminophenol | 0.30 g |
| Remcopal 334 | 22 g |
| Remcopal 349 | 22 g |
| Butylglycol | 8 g |
| Propylene glycol | 8 g |
| Ethylenediaminetetraacetic acid | 0.20 g |
| 35° Bé strength sodium bisulphite solution | 1 cc |
| 22° Bé strength ammonia solution | 10 cc |
| Water q.s.p. | 100 g |
| Composition $S_{12}$: | |
| 6-Aminobenzomorpholine | 0.50 g |
| Resorcinol | 0.45 g |
| Meta-aminophenol | 0.75 g |
| Remcopal 334 | 20 g |
| Remcopal 349 | 20 g |
| Carbopol 934 | 1.25 g |
| Absolute ethyl alcohol | 8 g |
| Propylene glycol | 6 g |
| Ethylenediaminetetraacetic acid | 0.2 g |
| 35° Bé strength sodium bisulphite solution | 0.5 cc |
| Citric acid q.s.p. | pH 6 |
| Water q.s.p. | 100 g |

40 g of the composition $S_{11}$ are mixed with 20 g of a 12% strength solution of hydrogen peroxide, before use, and the gel thus obtained is applied to a head of hair which is dyed chestnut.

After 15 minutes, 20 g of the composition $S_{12}$ are incorporated, whilst carefully massaging the hair, and this mixture is left in contact with the heat of hair for 10 minutes, after which time the hair is rinsed, shampooed and dried.

The hair is coloured deep chestnut when an ashen sheen, whereas, if the gelled mixture of 40 g of the composition $S_{11}$ with 20 g of the composition $S_{12}$ and 20 g of 12% strength hydrogen peroxide solution is applied for 30 minutes, this same head of hair is coloured a bluish chestnut which lacks background.

EXAMPLE NO. 9

The following dyeing composition is prepared:

| Composition $S_{13}$: | |
|---|---|
| N-($\beta$-Hydroxyethyl)-N-($\beta$-mesylaminoethyl)-para-phenylenediamine dihydrochloride monohydrate | 3.6 g |
| 4-N-[$\beta$-($\beta'$-Hydroxyethoxy)-ethyl]-aminoaniline sulphate | 1.5 g |
| Ortho-aminophenol | 0.5 g |
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| Thiolactic acid | 1.5 g |
| 22° Bé strength ammonia solution | 12 cc |
| Water q.s.p. | 100 g |

40 g of this composition are applied for 10 minutes to a head of hair which is dyed blond and unevenly sensitised and 40 g of the composition $S_4$ are then added without rinsing.

This dyeing mixture is thoroughly homogenised and, after 20 minutes, the hair is rinsed, shampooed and dried; it is coloured dull deep chestnut, whereas, under the same conditions, the mixture of the above two para-phenylenediamines colours this head of hair dull deep blond and ortho-aminophenol colours it golden deep blond.

EXAMPLE NO. 10

The following dyeing composition is prepared:

| Composition S₁₄: | |
|---|---|
| 4-Amino-N-ethyl-N-(α-carbamylmethyl)-aniline | 1.95 g |
| 2-N-(β-Hydroxyethyl)-aminoaniline hemi-sulphate | 0.60 g |
| Remcopal 334 | 21 g |
| Remcopal 349 | 24 g |
| Oleic acid | 4 g |
| Butylglycol | 3 g |
| Absolute ethyl alcohol | 14 g |
| Ethylenediaminetetraacetic acid | 0.2 g |
| α,α'-Dimercaptoadipic acid | 0.5 g |
| Cysteine hydrochloride | 0.1 g |
| Thioglycollic acid | 1 g |
| 22° Bé strength ammonia solution | 11 cc |
| Water q.s.p. | 100 g |

The thioglycollic acid is introduced at the time of use.

40 g of the composition $S_{14}$ are applied to a head of hair which is dyed blond.

After 10 minutes, 40 g of the composition $S_2$ are added, whilst carefully massaging the hair, and the mixture is left on the hair for a further 25 minutes. After rinsing, shampooing and then drying, the head of hair is coloured dull chestnut, whereas, if a composition which is identical except that it contains only one of the para and ortho compounds at a concentration of $1.3 \times 10^{-2}$ mol % is applied in the same manner, this head of hair is coloured ashen blond with the para-phenylenediamine and golden deep blond with the ortho-phenylenediamine.

EXAMPLE NO. 11

The following dyeing composition is prepared:

| Composition S₁₅: | |
|---|---|
| Ortho-aminophenol | 0.54 g |
| N-(β-Hydroxyethyl)-N-(β-mesylaminoethyl)-para-phenylenediamine dihydrochloride monohydrate | 3.46 g |
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| Thioglycollic acid | 1 g |
| 22° B strength ammonia solution | 11 g |
| Water q.s.p. | 100 g |
| pH: 10 | |

10 g of this composition are applied to naturally copper red light chestnut hair and, after 10 minutes, 5 g of an oxidising milk, containing 18% of hydrogen peroxide and having the composition $S_8$ above, are then added to the hair without rinsing beforehand.

The hair is massaged thoroughly. After an application time of 20 minutes, and after rinsing and shampooing, a slightly ashen deep chestnut coloration is obtained.

If the ortho-aminophenol is omitted from the dyeing composition, with the rest, namely the composition, application time, nature of the hair and the like, remaining the same, a golden deep blond coloration is obtained.

EXAMPLE NO. 12

The following dyeing composition is prepared:

| Composition S₁₆: | |
|---|---|
| Ortho-aminophenol | 0.22 g |
| 4-Amino-N-ethyl-N-(β-mesylaminoethyl)-aniline dihydrochloride | 2 g |
| Oxyethyleneated oleyl alcohol containing 2 mols of ethylene oxide | 4 g |
| Oxyethyleneated oleyl alcohol containing 4 mols of ethylene oxide | 4 g |
| Diethanolamides of copra fatty acids | 10 g |
| Nonylphenol containing 4 mols of ethylene oxide | 6 g |
| Nonylphenol containing 9 mols of ethylene oxide | 6 g |
| Masquol DTPA | 2 g |
| Propylene glycol | 8 g |
| 96° strength ethanol | 2 g |
| 35° Bé strength sodium bisulphite solution | 2 g |
| 22° Bé strength ammonia solution | 10 g |
| Water q.s.p. | 100 g |
| pH = 9.9 | |

40 g of this composition are mixed, before use, with 40 g of the 6% strength oxidising milk having the composition $S_{17}$ below.

| Composition S₁₇: | |
|---|---|
| Polychol 5 | 3.3 g |
| Polychol 20 | 1.7 g |
| Stearyl alcohol | 5 g |
| Hydrogen peroxide of 100 volumes strength | 20 g |
| Phosphoric acid q.s.p. | pH 2.3 |
| Water q.s.p. | 100 g |

This mixture is applied to bleached hair for 20 minutes. After rinsing and shampooing, a silvery blue-grey coloration is obtained.

If the ortho-aminophenol is omitted in the preceding example, with all the rest remaining unchanged, a very light blond with a green shade is obtained.

EXAMPLE NO. 13

The following dyeing composition is prepared:

| Composition S₁₈: | |
|---|---|
| 2-N-(β-Hydroxyethyl)-aminophenol | 0.153 g |
| N-(β-Mesylaminoethyl)-N-(β-hydroxyethyl)-para-phenylenediamine dihydrochloride monohydrate | 1.73 g |
| 2-Mercaptoethanol | 2 g |
| Remcopal 334 | 3 g |
| Remcopal 349 | 4 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Propylene glycol | 10 g |
| Carbopol 934 | 0.2 g |
| 35° Bé strength sodium bisulphite solution | 1 g |
| 22° Bé strength ammonia solution | 7 g |
| Trilon B | 0.1 g |
| Water q.s.p. | 100 g |
| pH = 10.1 | |

30 g of an oxidising milk containing 6% of hydrogen peroxide and having the composition $S_{19}$ defined below are added to 30 g of this composition at the time of use.

| Composition S₁₉: | |
|---|---|
| Polychol 5 | 3.3 g |
| Polychol 20 | 1.7 g |
| Stearyl alcohol | 5 g |
| Hydrogen peroxide of 100 volumes strength | 20 g |

| Composition S₁₉: | |
|---|---|
| Phosphoric acid q.s.p. | pH 2.3 |
| Water q.s.p. | 100 g |

This mixture is applied to an initially brown head of hair which has been bleached straw yellow. After 10 minutes, 5 g of the dyeing composition S₂₀ below are applied without any rinsing beforehand.

| Composition S₂₀: | |
|---|---|
| 2-Hydroxy-1,4-naphthoquinone | 6.7 g |
| Resorcinol | 2.3 g |
| Propylene glycol q.s.p. | 100 g |

The head of hair is thoroughly massaged so as to achieve a good homogenisation. After an application time of 20 minutes, and after rinsing and shampooing, a golden chestnut coloration is obtained.

If the 2-N-(β-hydroxyethyl)-aminophenol is omitted from the dyeing composition S₁₈ in the above example, with the rest, namely the compositions, application time and nature of the hair, remaining identical, a golden blond coloration is then obtained.

EXAMPLE NO. 14

The following dyeing composition is prepared:

| Composition S₂₁: | |
|---|---|
| 4-amino-N-ethyl-N-(β-mesylaminoethyl)-aniline dihydrochloride | 3.3 g |
| Ortho-aminophenol | 0.54 g |
| Remcopal 334 | 21 g |
| Remcopal 349 | 24 g |
| Oleic acid | 3 g |
| Absolute ethyl alcohol | 14 g |
| Ethylenediaminetetraacetic acid | 0.2 g |
| Thioglycollic acid | 1.7 g |
| Ammonia solution (d = 0.92) | 12 ml |
| Water q.s.p. | 100 g |
| pH = 9.6 | |

10 g of this composition are applied to naturally golden blond hair and, after an application time of 5 minutes, 5 g of an oxidising milk containing 9% of hydrogen peroxide and having the composition S₂₂ below are then added to the hair without rinsing beforehand.

| Composition S₂₂: | |
|---|---|
| Polychol 5 | 3.3 g |
| Polychol 20 | 1.7 g |
| Stearyl alcohol | 5 g |
| Hydrogen peroxide of 100 volumes strength | 30 g |
| Phosphoric acid q.s.p. | pH 2.8 |
| Water q.s.p. | 100 g |

The hair is thoroughly massaged in order to achieve a good homogenisation and, after an application time of 5 minutes, 5 g of the following dyeing composition S₂₃:

| Composition S₂₃: | |
|---|---|
| 2-Methyl-5-aminophenol | 0.49 g |
| Remcopal 334 | 20 g |
| Remcopal 349 | 20 g |
| Carbopol 934 | 1.25 g |

| Composition S₂₃: | |
|---|---|
| Propylene glycol | 6 g |
| Ethylene glycol distearate | 0.58 g |
| Ethylenediaminetetraacetic acid | 0.2 g |
| 35° Bé strength sodium bisulphite solution | 0.5 g |
| Citric acid q.s.p. | pH 6 |
| Water q.s.p. | 100 g | are then added to the hair without rinsing beforehand.

After a good homogenisation and an application time of 30 minutes, the hair is rinsed and shampooed.

A black violet coloration is obtained.

If the ortho-aminophenol is omitted from the dyeing composition S₂₁ in the above example, with the rest namely the composition application time and nature of the hair, remaining unchanged, a light beige grey coloration with a purple shade is obtained.

EXAMPLE NO. 15

The following dyeing composition is prepared:

| Composition S₂₄: | |
|---|---|
| N,N-bis-(β-Hydroxyethyl)-para-phenylenediamine sulphate | 1 g |
| 2-N-(β-Hydroxyethyl)-aminophenol | 0.5 g |
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| Thiolactic acid | 1 g |
| 22° Bé strength ammonia solution | 11 g |
| Water q.s.p. | 100 g |
| pH = 10 | |

10 g of an oxidising milk containing 6% of hydrogen peroxide and having the composition S₂₅ below are added to 10 g of the above composition.

| Composition S₂₅: | |
|---|---|
| Polychol 5 | 3.3 g |
| Polychol 20 | 1.7 g |
| Stearyl alcohol | 5 g |
| Hydrogen peroxide of 100 volumes strength | 20 g |
| Phosphoric acid q.s.p. | pH 2.8 |
| Water q.s.p. | 100 g |

After a good homogenisation, this mixture is applied to hair which is dyed copper red. After an application time of 15 minutes, and after rinsing and shampooing, a dull deep chestnut coloration is obtained.

EXAMPLE NO. 16

The following dyeing composition is prepared:

| Composition S₂₆: | |
|---|---|
| N-(β-mesylaminoethyl)-N-(β-hydroxyethyl)-para-phenylenediamine dihydrochloride monohydrate | 3.6 g |
| Ortho-aminophenol | 0.5 g |
| 3-Nitro-4-N'-(β-hydroxyethyl)-amino-N,N-(β-hydroxyethyl)-aniline | 0.8 g |
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| Thioglycollic acid | 1 g |
| 22° Bé strength ammonia solution | 11 g |

| Composition S26: | |
|---|---|
| Water q.s.p. | 100 g |

15 g of this mixture are applied to the roots of a golden blond head of hair which has been permed 4 months previously. After 8 minutes, 15 g of this same mixture are distributed over the whole of the head of hair and, after two minutes, 30 g of an oxidising milk containing 9% of hydrogen peroxide and having the following composition S27:

| Composition S27: | |
|---|---|
| Polychol 5 | 3.3 g |
| Polychol 20 | 1.7 g |
| Stearyl alcohol | 5 g |
| Hydrogen peroxide of 100 volumes strength | 30 g |
| Phosphoric acid q.s.p. | pH 2.8 |
| Water q.s.p. | 100 g | are added to the entire head of hair, whilst massaging thoroughly in order to obtain a good homogenisation.

After an application time of 20 minutes, and after rinsing and shampooing, a uniform black coloration with a violet sheen is obtained.

If the ortho-aminophenol is omitted with the rest of the method of application remaining unchanged, a deep chestnut with a purple-violet sheen is obtained.

EXAMPLE NO. 17

The following dyeing composition is prepared:

| Composition S28: | |
|---|---|
| N-(β-Mesylaminoethyl)-N-(β-hydroxyethyl)-para-phenylenediamine dihydrochloride | 1.09 g |
| 2-N-(β-Hydroxyethyl)-aminophenol | 0.153 g |
| Remcopal 334 | 12 g |
| Remcopal 349 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| Propylene glycol | 6 g |
| 35° Bé strength sodium bisulphite solution | 1.2 g |
| Trilon B | 0.12 g |
| Mercaptosuccinic acid | 1.8 g |
| 22° Bé strength ammonia solution | 10 g |
| Water q.s.p. | 100 g |
| pH = 10.1 | |

25 g of this composition are applied to a naturally straw-coloured head of hair.

After an application time of 10 minutes, 20 g of an oxidising milk containing 9% of hydrogen peroxide and having the composition S27 defined above are added to the head of hair without rinsing beforehand.

The hair is massaged thoroughly in order to achieve a good homogenisation and, after an application time of 10 minutes, 21 g of the dyeing composition S29 are then added to the head of hair without rinsing beforehand, the composition being distributed as well as possible.

| Composition S29: | |
|---|---|
| 2-Methyl-5-amino-6-nitrophenol | 0.15 g |
| 3-Nitro-4-N-(β-hydroxyethyl)-aminophenol | 0.2 g |
| Oxyethyleneated oleyl alcohol containing 2 mols of ethylene oxide | 5 g |
| Oxyethyleneated oleyl alcohol containing 4 mols of ethylene oxide | 10 g |
| Propylene glycol | 10 g |
| Triethanolamine q.s.p. | pH = 7 |
| Water q.s.p. | 100 g |

After an application time of 15 minutes, and after rinsing and shampooing, a very ashen chestnut coloration is obtained.

If the 2-N-(β-hydroxyethyl)-aminophenol is omitted from the dyeing composition S28, with all the rest of the description remaining unchanged, a golden very light chestnut is obtained.

EXAMPLE NO. 18

The following dyeing composition is prepared:

| Composition S30: | |
|---|---|
| Ortho-aminophenol | 0.54 g |
| 4-N-Ethyl-N-(β-mesylaminoethyl)-aminoaniline dihydrochloride | 3.72 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| Thioglycollic acid | 0.17 g |
| 35° Bé strength sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |
| pH = 9.5 | |

10 g of this composition are applied to 90% naturally white hair and, after an application time of 10 minutes, 5 g of an oxidising milk containing 18% of hydrogen peroxide and having the composition S8 are then added to the hair without rinsing beforehand.

The hair is massaged thoroughly in order to achieve a good homogenisation and, after an application time of 25 minutes, 5 g of the following dyeing composition S31:

| Composition S31: | |
|---|---|
| 3-Nitro-4-N-(β-hydroxyethyl)-aminophenol | 1.02 g |
| Remcopal 334 | 12 g |
| Remcopal 349 | 15 g |
| Oxyethylenated oleyl alcohol containing 2 mols of ethylene oxide | 1.5 g |
| Oxyethyleneated oleyl alcohol containing 4 mols of ethylene oxide | 1.5 g |
| Propylene glycol | 6 g |
| 35° Bé sodium bisulphite solution | 1.2 g |
| Trilon B | 0.12 g |
| Triethanolamine q.s.p. | pH = 6.5 |
| Water q.s.p. | 100 g | are then added to the hair without rinsing beforehand.

After a good homogenisation and an application time of 5 minutes, the hair is rinsed and washed. A very dark violet coloration is obtained.

If the ortho-aminophenol is omitted with all the rest of the description remaining unchanged, a bronze green coloration is obtained.

EXAMPLE NO. 19

The following dyeing composition is prepared:

| Composition S₃₂: | |
|---|---|
| 2-N-(β-Hydroxyethyl)-aminophenol | 0.31 g |
| 4-N-Ethyl-N-(β-mesylaminoethyl)-aminoaniline dihydrochloride | 1.98 g |
| Hydroxyethylcellulose | 1 g |
| Butylglycol | 5 g |
| Ammonium acetate | 4 g |
| Ammonium lauryl-sulphate | 0.1 g |
| 22°Bé strength ammonia solution | 10 g |
| Water q.s.p. | 100 g |
| ph = 9.8 | |

100 g of hydrogen peroxide of 20 volumes strength are added at the time of use.

When applied to 90% naturally white hair for 20 minutes at 20° C., this mixture imparts to the hair, after rinsing and shampooing, a silver grey coloration.

If the ortho compound is omitted from the composition S₃₂, whilst keeping the rest of the composition and also the method of application unchanged, a light yellow coloration is obtained.

EXAMPLE NO. 20

The following dyeing composition is prepared:

| Composition S₃₃: | |
|---|---|
| 2-N-(β-Hydroxyethyl)-aminophenol | 0.6 g |
| N-(β-Hydroxyethyl)-N-(β-mesylaminoethyl)-para-phenylenediamine dihydrochloride monohydrate | 4 g |
| Sodium lauryl-sulphate containing 19% of starting oxyethyleneated alcohol | 20 g |
| Trilon B | 0.1 g |
| Triethanolamine | 10 g |
| Thioglycollic acid | 0.5 g |
| Water q.s.p. | 100 g |
| ph = 8.1 | |

100 g of hydrogen peroxide of 20 volumes strength are added at the time of use.

When applied to bleached hair for 20 minutes at 25° C., this mixture imparts to the hair, after rinsing and shampooing, a very dark grey coloration.

If the ortho compound is omitted in this example, whilst keeping the rest of the composition and also the method of application unchanged, a fairly dark petroleum green coloration is obtained.

EXAMPLE NO. 21

The following dyeing composition is prepared:

| Composition S₃₄: | |
|---|---|
| N,N'-(β-Hydroxyethyl)-N,N'-(4-aminophenyl)-tetramethylenediamine tetrahydrochloride | 2 g |
| Ortho-aminophenol | 0.2 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| 35° Bé strength sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |

| Composition S₃₄: | |
|---|---|
| ph = 9.8 | |

100 g of hydrogen peroxide of 20 volumes strength are added at the time of use.

This mixture is applied to 90% naturally white hair. After an application time of 20 minutes, and after rinsing and shampooing, a blue grey coloration is obtained.

If the ortho-aminophenol is omitted in this example, with the rest of the description remaining unchanged, a silvery pale green coloration is obtained.

EXAMPLE NO. 22

The following dyeing composition is prepared:

| Composition S₃₅: | |
|---|---|
| 2,6-Dimethyl-3-methoxy-para-phenylenediamine dihydrochloride | 2.39 g |
| Ortho-diphenol | 0.83 g |
| Alfol C 16/18 E | 7.2 g |
| Lanette wax E | 0.45 g |
| Cemulsol B | 0.9 g |
| Oleyl diethanolamide | 1.35 g |
| Masquol DTPA | 2.25 g |
| 22° Bé strength ammonia solution | 10 g |
| Water q.s.p. | 100 g |

100 g of hydrogen peroxide of 20 volumes strength are added at the time of use.

This mixture is applied to bleached white hair for 20 minutes. After rinsing and shampooing, a grey coloration with a green shade is obtained.

If the ortho-diphenol is omitted in this example, with the rest of the description remaining unchanged, virtually no coloration is imparted to the initial bleached hair.

EXAMPLE NO. 23

The following dyeing composition is prepared:

| Composition S₃₆: | |
|---|---|
| 4-N-Ethyl-(β-mesylaminoethyl)-aminoaniline dihydrochloride | 3.31 g |
| Ortho-diphenol | 1.10 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| 35° Bé sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |
| ph = 10 | |

100 g of hydrogen peroxide of 20 volumes strength are added at the time of use.

This mixture is applied to bleached white hair; after an application time of 20 minutes, and after rinsing and shampooing, a deep blue grey coloration is obtained.

If the ortho-diphenol is omitted from the preceding dyeing composition, with all the rest of the description remaining unchanged, a light bronze green coloration is obtained.

EXAMPLE NO. 24

The following dyeing composition is prepared:

| Composition S₃₇: | |
|---|---|
| 4-N-Ethyl-N-(β-mesylaminoethyl)-aminoaniline dihydrochloride | 3.30 g |
| Ortho-diphenol | 1.10 g |
| Alfol C 16/18 E | 8 g |
| Lanette wax E | 0.5 g |
| Cemulsol B | 1 g |
| Oleyl diethanolamide | 1.5 g |
| Masquol DTPA | 2.5 g |
| 22° Bé strength ammonia solution | 11 g |
| 2-Mercaptoethanol | 1.7 g |
| Water q.s.p. | 100 g |
| pH = 9.6 | |

50 g of this composition are applied to 90% white hair. After an application time of 10 minutes, 50 g of an oxidising milk containing 6% of hydrogen peroxide and having the composition S₁₇ described in Example 12 are added to the hair without rinsing beforehand.

The hair is thoroughly massaged in order to achieve a good homogenisation. After an application time of 10 minutes, 45 g of the following dyeing composition S₃₈:

| Composition S₃₈: | |
|---|---|
| 6-Aminobenzomorpholine dihydrochloride | 0.05 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O₁₂ | 4.5 g |
| Diethanolamides of copra fatty acids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g | are added.

The hair is thoroughly massaged. After an application time of 10 minutes, and after rinsing and shampooing, a blue black coloration is obtained.

If the ortho-diphenol is omitted from the dyeing composition S₃₇, with all the rest of the description remaining unchanged, a bottle green coloration is obtained.

EXAMPLE NO. 25

The following dyeing composition is prepared:

| Composition S₃₉: | |
|---|---|
| 4-N-Ethyl-N-(β-piperidincethyl)-aminoaniline trihydrochloride | 2.5 g |
| Ortho-diphenol | 0.2 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 35° Bé strength sodium bisulphite solution | 1 g |
| Trilon B | 0.1 g |
| Water q.s.p. | 100 g |
| pH = 9.7 | |

5 g of an oxidising milk containing 18% of hydrogen peroxide and having the composition S₈ described in Example 6 are added to 10 g of this dyeing composition at the time of use. This mixture is applied to bleached white hair.

After an application time of 15 minutes, 5 g of the following dyeing composition S₄₀:

| Composition S₄₀: | |
|---|---|
| 2-Methyl-5-N-(β-hydroxyethyl)-aminophenol | 0.3 g |
| 2-N-(β-Hydroxyethyl)-amino-5-nitroanisole | 0.12 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 35° Bé strength sodium bisulphite solution | 1 g |
| Trilon B | 0.1 g |
| Water q.s.p. | 100 g |
| pH = 9.7 | | are applied to the hair without rinsing beforehand.

The hair is thoroughly massaged. After an application time of 10 minutes, and after rinsing and shampooing, a tin grey coloration is obtained.

If the ortho-diphenol is omitted from the dyeing composition S₃₉ in this example, with all the rest of the description remaining unchanged, a pinkish beige coloration is obtained.

EXAMPLE NO. 26

The following dyeing composition is prepared:

| Composition S₄₁: | |
|---|---|
| 4-N-Ethyl-N-(α-carbamylmethyl)-aminoaniline | 2.12 g |
| Ortho-diphenol | 0.54 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 2-Mercaptoethanol | 2 g |
| 35° Bé strength sodium bisulphite solution | 1 g |
| Trilon B | 0.1 g |
| 22° Bé strength ammonia solution | 7 g |
| Water q.s.p. | 100 g |
| pH = 9.7 | |

20 g of this composition are applied to naturally straw blond hair.

After an application time of 5 minutes, 5 g of an oxidising milk containing 18% of hydrogen peroxide and having the composition S₈ described in Example 6 are added to the hair without rinsing beforehand.

After having thoroughly massaged the hair in order to achieve a good homogenisation. The mixture is left on the hair for 20 minutes and the hair is then rinsed and washed. A black brown coloration is obtained. If the ortho-diphenol is omitted from the preceding composition, with all the rest of the description remaining unchanged, a light chestnut coloration is obtained.

EXAMPLE NO. 27

The following dyeing composition is prepared:

| Composition S$_{42}$: | |
|---|---|
| N,N'-(β-Hydroxyethyl)-N,N'-(4-aminophenyl)-tetramethylenediamine tetrahydrochloride | 3.8 g |
| Ortho-diphenol | 0.28 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| Thioglycollic acid | 0.2 g |
| 35° Bé strength sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |
| pH = 10.2 | |

10 g of this composition are applied to naturally light chestnut hair.

After an application time of 8 minutes, 10 g of an oxidising milk containing 9% of hydrogen peroxide and having the composition S$_{27}$ described in Example 16 are added to the hair without rinsing beforehand.

The hair is thoroughly massaged in order to achieve a good homogenisation. After an application time of 10 minutes, and after rinsing and shampooing, a black brown coloration with a purple-violet shade is obtained.

If the ortho-diphenol is omitted from the dyeing composition in this example, whilst keeping the rest of the description unchanged, a dark green coloration is obtained.

EXAMPLE NO. 28

The following dyeing composition is prepared:

| Composition S$_{43}$: | |
|---|---|
| N,N'-(β-Hydroxyethyl)-N,N'-(4-aminophenyl)-propylenediamine tetrahydrochloride | 4.15 g |
| Ortho-diphenol | 0.33 g |
| 2-Nitro-4-N',N'-(β-hydroxyethyl)-amino-N-(β-hydroxyethyl)-aniline | 0.50 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| 35° Bé strength sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |
| pH = 9.6 | |

100 g of hydrogen peroxide of 20 volumes strength are added at the time of use.

When applied to naturally golden blond hair for 20 minutes, this mixture imparts to the hair, after rinsing and shampooing, an ashen deep chestnut coloration with a purple-violet sheen.

If the ortho-diphenol is omitted in this example, with the rest of the description unchanged, a green-yellow coloration is obtained.

EXAMPLE NO. 29

The following dyeing composition is prepared:

| Composition S$_{44}$: | |
|---|---|
| N,N'-(β-Hydroxyethyl (4-aminophenyl)-tetramethylenediamine tetrahydrochloride | 2.07 g |
| Ortho-diphenol | 0.33 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O$_{12}$ | 4.5 g |
| Diethanolamides of copra fatty acids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g |
| pH: 10 | |

100 g of hydrogen peroxide of 20 volumes strength are added at the time of use.

This mixture is applied to hair which is bleached white. After an application time of 20 minutes, and after rinsing and shampooing, a silvery blue grey coloration is obtained.

If the ortho-diphenol is omitted in this example, with the rest of the description remaining unchanged, a light bronze green coloration is obtained.

EXAMPLE NO. 30

The following dyeing composition is prepared:

| Composition S$_{45}$: | |
|---|---|
| 4-N,N-bis-(β-Hydroxyethyl)-para-phenylenediamine sulphate | 3.03 g |
| Ortho-diphenol | 0.33 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O$_{12}$ | 4.5 g |
| Diethanolamides of copra fatty aids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g |
| pH = 10 | |

100 g of hydrogen peroxide of 20 volumes strength are added at the time of use.

When applied to bleached white hair for 20 minutes at ambient temperature, this mixture imparts to the hair, after rinsing and shampooing, a deep blue grey coloration.

If the ortho-diphenol is omitted in this example, with the rest of the description remaining identical, a light bronze green coloration is obtained.

EXAMPLE NO. 31

The following dyeing composition is prepared:

| Composition S$_{46}$: | |
|---|---|
| N-(β-Hydroxyethyl)-N-(β-mesylaminoethyl)-para-phenylenediamine dihydrochloride monohydrate | 1.73 g |
| Ortho-diphenol | 0.275 g |
| Oxyethyleneated oleyl alcohol containing 2 mols | |

| Composition S₄₆: | |
|---|---|
| of ethylene oxide | 4.5 g |
| Oxyethyleneated oleyl alcohol containing 4 mols of ethylene oxide | 4.5 g |
| Diethanolamides of copra fatty acids | 10 g |
| 35° Bé strength sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |
| pH = 10.2 | |

60 g of hydrogen peroxide of 20 volumes strength are added at the time of use.

When applied for 25 minutes to hair which is bleached very golden straw blond, this mixture imparts to the hair, after rinsing and shampooing, a smoke grey coloration.

If the ortho-diphenol is omitted in this example, with the rest of the description remaining unchanged, a mustard coloration is obtained.

EXAMPLE NO. 32

The following dyeing composition $S_{47}$ is prepared:

| Composition S₄₇: | |
|---|---|
| 4-Amino-N-ethyl-N-mesylaminoethyl aniline dihydrochloride | 3.3 g |
| Ortho-aminophenol | 0.33 g |
| 2-Hydroxyethylamino-5-methyl-4,4'-dihydroxy-diphenylamine | 0.66 g |
| Remcopal 334 | 21 g |
| Remcopal 349 | 24 g |
| Oleic acid | 4 g |
| Butylglycol | 3 g |
| Absolute ethyl alcohol | 14 g |
| Masquol DTPA | 2.5 g |
| Sodium sulphite | 1 g |
| Glycerol thioglycollate | 1.5 g |
| Sodium bicarbonate | 0.4 g |
| Sodium hydroxide | 0.1 g |
| 22° Bé strength ammonia solution | 10 cm³ |
| Water q.s.p. | 100 g |

The mercaptan is introduced at the time of use.

40 g of the composition $S_{47}$ are applied to a head of hair which has been dyed blond 2 months previously by oxidative coloration.

After 10 minutes, 40 g of the composition $S_2$ are added without rinsing and left in contact with the head of hair for a further 20 minutes.

After rinsing, shampooing and drying, the hair is uniformly coloured slightly pearlescent deep chestnut, whereas the same composition, applied in a conventional manner for 30 minutes, colours this head of hair blond at the roots and brown at the sensitised parts.

EXAMPLE NO. 33

The following dyeing composition is prepared:

| Composition S₄₈: | |
|---|---|
| 4-Amino-N-ethyl-N-mesylaminoethylaniline dihydrochloride | 3.3 g |
| Ortho-aminophenol | 0.33 g |
| 2-Hydroxyethylamino-5-methyl-4,4'-dihydroxy-diphenylamine | 0.66 g |
| Remcopal 334 | 21 g |
| Remcopal 349 | 24 g |
| Oleic acid | 4 g |
| Butylglycol | 3 g |
| Absolute ethyl alcohol | 14 g |
| Masquol DTPA | 2.5 g |
| Sodium sulphite | 1 g |
| Glycerol thioglycollate | 1.5 g |
| Sodium bicarbonate | 0.4 g |
| Sodium hydroxide | 0.1 g |
| 22° Bé strength ammonia solution | 10 cm³ |
| Water q.s.p. | 100 g |

The mercaptan can be introduced at the time of use.

40 g of the composition $S_{48}$ are applied to a head of hair which has been dyed blond 2 months previously by oxidative coloration.

After 10 minutes, 40 g of the composition $S_2$ are added without rinsing and left in contact with the head of hair for a further 20 minutes.

After rinsing, shampooing and drying, the hair is uniformly coloured slightly pearlescent deep chestnut, whereas the same composition, applied in a conventional manner for 30 minutes, colours this head of hair blond at the roots and brown at the sensitised parts.

EXAMPLE NO. 34

The following dyeing composition is prepared:

| Composition S₄₉: | |
|---|---|
| 4-N-(β-Mesylaminoethyl)-aminoaniline sulphate | 1.98 g |
| Ortho-aminophenol | 0.25 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O₁₂ | 4.5 g |
| Diethanolamides of copra fatty acids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g |
| pH = 10 | |

80 g of hydrogen peroxide of 20 volumes strength are added at the time of use. When applied to 90% naturally white hair for 20 minutes at ambient temperature, this mixture imparts to the hair, after rinsing and shampooing, an ashen gray coloration; if the ortho-aminophenol is omitted in this example, with the rest of the description remaining identical, a beige coloration is obtained.

EXAMPLE NO. 35

The following dyeing composition is prepared:

| Composition S₅₀: | |
|---|---|
| 4-N-(β-Hydroxyethyl)-amino-3-chloroaniline sulphate | 2.84 g |
| Ortho-aminophenol | 0.83 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 35° Bé strength sodium bisulphite solution | 1 g |
| Trilon B | 0.1 g |

-continued

| Composition S₅₀: | |
|---|---|
| 22° Bé strength ammonia solution | 7 g |
| Water q.s.p. | 100 g |
| pH = 10.0 | |

100 g of H₂O₂ of 20 volumes strength are added at the time of use.

When applied to 90% naturally white hair for 25 minutes, this mixture imparts to the hair, after rinsing and shampooing, a light ashen grey coloration; if the ortho-aminophenol is omitted in this example, with the rest of the description remaining unchanged, virtually no coloration is imparted to the initial hair.

EXAMPLE NO. 36

The following dyeing composition is prepared:

| Composition S₅₁: | |
|---|---|
| 4-N-Ethyl-N-(β-mesylaminoethyl)-amino-2-methylaniline sulphate monohydrate | 4.36 g |
| Ortho-diphenol | 1.10 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| 35° Bé strength sodium bisulphite solution | 1 g |
| Masquol DTPA | 2 g |
| Propylene glycol | 4.5 g |
| Butylglycol | 8 g |
| 96° strength ethanol | 8 g |
| 22° Bé strength ammonia solution | 10 g |
| Water q.s.p. | 100 g |
| pH = 10.2 | |

100 g of H₂O₂ of 20 volumes strength are added at the time of use.

When applied to bleached hair for 20 minutes at ambient temperature, this mixture imparts to the hair, after rinsing and shampooing, a tin coloration; if the orthodiphenol is omitted in this example, with the rest of the description remaining unchanged, a very light pinkish beige coloration is obtained.

EXAMPLE No. 37

The following dyeing composition is prepared:

| Composition S₅₂: | |
|---|---|
| 4-N-Ethyl-N-(β-mesylaminoethyl)-aminoaniline dihydrochloride | 3.3 g |
| Ortho-aminophenol | 0.3 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 35° Bé strength sodium bisulphite solution | 0.1 g |
| Trilon B | 7 g |
| 22° Bé strength ammonia solution 7 g | |
| Water q.s.p. | 100 g |
| pH = 9.7 | |

10 g of H₂O₂ of 20 volumes strength are added to 10 g of this dyeing composition at the time of use.

This mixture is applied to bleached white hair for 15 minutes.

After this application time, 5 g of the following dyeing composition S₅₃:

| Composition S₅₃: | |
|---|---|
| 2,6-Siaminopyridine | 0.24 g |
| Resorcinol | 0.45 g |
| Meta-aminophenol | 0.75 g |
| Remcopal 334 | 12 g |
| Remcopal 349 | 15 g |
| Oxyethyleneated oleyl alcohol containing 2 mols of ethylene oxide | 1.5 g |
| oxyethyleneated oleyl alcohol containing 4 mols of ethylene oxide | 1.5 g |
| Propylene glycol | 6 g |
| 35° Bé sodium bisulphite solution | 1.2 g |
| Trilon B | 0.12 g |
| Triethanolamine q.s.p. | pH = 6.8 |
| Water q.s.p. | 100 g | are applied without rinsing beforehand.

The hair is thoroughly massaged. After an application time of 10 minutes, and after rinsing and shampooing, a metallic dark blue grey coloration is obtained.

If the ortho-aminophenol is omitted in this example, with the rest of the description remaining unchanged, a blue green coloration is obtained.

EXAMPLE NO. 38

10 g of the composition S₅₂ are applied to 90% naturally white hair for 15 minutes. 10 g of H₂O₂ of 20 volumes strength are then added without rinsing beforehand, whilst thoroughly massaging the hair, and it is left in contact with the hair for 10 minutes.

5 g of the following dyeing composition:

| Composition S₅₄: | |
|---|---|
| 2,6-Dimethyl-5-acetaminophenol | 0.48 g |
| Resorcinol | 0.45 g |
| Meta-aminophenol | 0.75 g |
| Remcopal 334 | 12 g |
| Remcopal 349 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| Propylene glycol | 6 g |
| 35° Bé strength sodium bisulphite solution | 1.2 g |
| Trilon B | 0.12 g |
| Methanolamine q.s.p. | pH = 6.8 |
| Water q.s.p. | 100 g | are then applied.

After a good homogenisation and an application time of 10 minutes, the hair is rinsed and washed.

A steel gray coloration is obtained; if the orthoaminophenol is omitted in this example, with the rest of the description remaining unchanged, a light grey coloration is obtained.

EXAMPLE NO. 39

The following dyeing composition is prepared:

| Composition S₅₅: | |
|---|---|
| 4-N-Ethyl-N-(β-mesylaminoethyl)-aminoaniline dihydrochloride | 3.3 g |
| Ortho-diphenol | 1.1 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen C₁₂ | 4.5 g |

-continued

| Composition S$_{55}$: | |
|---|---|
| Diethanolamides of copra fatty acids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g |
| pH = 10.0 | |

10 g of this composition are applied to 90% naturally white hair. After an application time of 10 minutes, 10 g of H$_2$O$_2$ of 20 volumes strength are added to the hair without rinsing beforehand. The hair is thoroughly massaged. After an application time of 10 minutes, 10 g of the following dyeing composition:

| Composition S$_{56}$: | |
|---|---|
| 2,4-Diaminophenoxyethanol dihydrochloride | 0.08 g |
| Remcopal 334 | 12 g |
| Remcopal 349 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| Propylene glycol | 6 g |
| 35° Bé strength sodium bisulphite solution | 1.2 g |
| Trilon B | 0.12 g |
| Triethanolamine q.s.p. | pH = 6.8 |
| Water q.s.p. | 100 g | are added.

The hair is thoroughly massaged. After an application time of 15 minutes and after rinsing and shampooing, a light blue gray coloration is obtained; if the ortho-diphenol is omitted in this example, with the rest of the description remaining unchanged, a blue coloration is obtained.

EXAMPLE NO. 40

10 g of the composition S$_{55}$ are applied to bleached hair. After an application time of 10 minutes, 10 g of H$_2$O$_2$ of 20 volumes strength are added to the hair without rinsing beforehand. The hair is thoroughly massaged in order to achieve a good homogenisation. After an application time of 10 minutes, 10 g of the following dyeing composition:

| Composition S$_{57}$: | |
|---|---|
| α-Naphthol | 0.035 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O$_{12}$ | 4.5 g |
| Diethanolamides of copra fatty acids | 9 g |
| Propylene glycol | 3.6 g |
| Butylglycol | 8 g |
| 96° strength ethanol | 5.4 g |
| 35° Bé strength Na bisulphite solution | 1 g |
| 22° Bé strength ammonia solution | 10 g |
| Water q.s.p. | 100 g | are added.

The hair is thoroughly massaged. After an application time of 10 minutes and after rinsing and shampooing, an anthracite grey coloration is obtained.

If the ortho-diphenol is omitted in this example, with the rest of the description remaining unchanged, a light bronze green coloration is obtained.

EXAMPLE NO. 41

The following dyeing composition is prepared:

| Composition S$_{58}$: | |
|---|---|
| 4-N-Ethyl-N-(β-mesylaminoethyl)-aminoaniline dihydrochloride | 3.3 g |
| Ortho-aminophenol | 0.3 g |
| 4,4′-Diaminodiphenylamine sulphate | 0.3 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 10 g |
| 35° Bé strength sodium bisulphite solution | 1 g |
| Masquol DTPA | 2 g |
| Propylene glycol | 4.5 g |
| Butylglycol | 8 g |
| 22° Bé strength ammonia solution | 10 g |
| Water q.s.p. | 100 g |

10 g of this mixture are applied to bleached white hair for 10 minutes. 10 g of hydrogen peroxide of 20 volumes strength are then added. The hair is thoroughly massaged and kept at ambient temperature for 20 minutes. After rinsing and shampooing, a very dark grey coloration with a violet sheen is obtained.

If the ortho-aminophenol is omitted in this example, with the rest of the description remaining unchanged, an ashen medium chestnut coloration is obtained.

EXAMPLE NO. 42

The following dyeing composition is prepared:

| Composition S$_{59}$: | |
|---|---|
| 4-N-Ethyl-N-(β-mesylaminoethyl)-aminoaniline dihydrochloride | 3.3 g |
| Ortho-aminophenol | 0.33 g |
| 2-Amino-5-methyl-4-hydroxy-4′-N-methylamino diphenylamine | 0.66 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 25° Bé strength sodium bisulphite solution | 1 g |
| Trilon B | 0.1 g |
| 22° Bé strength ammonia solution | 7 g |
| Water q.s.p. | 100 g |
| pH = 9.7 | |

10 g of this composition are applied to 90% naturally white hair. After 10 minutes, 10 g of H$_2$O$_2$ of 20 volumes strength are added without rinsing beforehand and left in contact with the hair for a further 20 minutes.

This mixture imparts to the hair, after rinsing and shampooing, a smoky grey coloration with a purple-violet sheen.

If the ortho-aminophenol is omitted in this example, with the rest of the description remaining unchanged, a light ashen beige coloration is obtained.

EXAMPLE NO. 43

The following dyeing composition is prepared:

| Composition S₆₀: | |
|---|---|
| 4-N-Ethyl-N-(α-carbamylethyl)-aminoaniline monohydrochloride | 1.95 g |
| 2-N-(β-Methoxyethyl)-aminoaniline monohydrochloride | 0.57 g |
| Oxyethyleneated oleyl alcohol containing 2 mols of ethylene oxide | 2.5 g |
| Oxyethyleneated oleyl alcohol containing 4 mols of ethylene oxide | 2.5 g |
| Remcopal 334 | 3 g |
| Remcopal 349 | 4 g |
| Propylene glycol | 10 g |
| Carbopol 934 | 0.2 g |
| 35° Bé strength sodium bisulphite solution | 1 g |
| Trilon B | 0.1 g |
| 22° Bé strength ammonia solution | 7 g |
| Water q.s.p. | 100 g |
| pH = 9.7 | |

10 g of this composition are applied to 90% naturally white hair and, after 10 minutes, 6 g of $H_2O_2$ of 20 volumes strength are added, whilst thoroughly massaging the hair, and the mixture is left on the hair for a further 20 minutes.

After rinsing and shampooing, a silvery mouse grey coloration is obtained.

If the 2-N-(β-methoxyethyl)-aminoaniline hydrochloride is omitted in this example, with the rest of the description remaining unchanged, a light bronze coloration is obtained.

EXAMPLE NO. 44

The following dyeing composition is prepared:

| Composition S₆₁: | |
|---|---|
| 4-N-Ethyl-N-(β-hydroxyethyl)-aminoaniline sulphate | 2.78 g |
| Ortho-diphenol | 0.50 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O₁₂ | 4.5 g |
| Diethanolamides of copra fatty acids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g |
| pH = 10.0 | |

100 g of hydrogen peroxide of 20 volumes strength are added at the time of use. When applied to 90% naturally white hair for 20 minutes at ambient temperature, this mixture imparts to the hair, after rinsing and shampooing, a steel grey coloration.

If the o-aminophenol is omitted in this example, with the rest of the description remaining unchanged, a light beige grey coloration is obtained.

EXAMPLE NO. 45

The following dyeing composition is prepared:

| Composition S₆₂: | |
|---|---|
| 4-N-Ethyl-N-(β-hydroxyethyl)-aminoaniline sulphate | 2.78 g |
| Ortho-aminophenol | 0.654 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen O₁₂ | 4.5 g |
| Diethanolamides of copra fatty acids | 9 g |
| Propylene glycol | 3.6 g |
| Butylglycol | 8 g |
| 96° strength ethanol | 5.4 g |
| 35° Bé strength sodium bisulphite solution | 1 g |
| 22° Bé strength ammonia solution | 10 g |
| Water q.s.p. | 100 g |
| pH = 10.0 | |

100 g of hydrogen peroxide of 20 volumes strength are added at the time of use. When applied to 90% naturally white hair for 20 minutes at ambient temperature, this mixture imparts to the hair, after rinsing and shampooing, a silvery grey coloration.

If the o-aminophenol is omitted in this example, with the rest of the description remaining unchanged, a light beige grey coloration is obtained.

The commercial products mentioned in the above examples have the following meanings:

Remcopal 334: Denotes oxyethyleneated nonylphenol containing 4 mols of ethylene oxide, sold by the Company Gerland.

Remcopal 349: Denotes oxyethyleneated nonylphenol containing 9 mols of ethylene oxide, sold by the Company Gerland.

Masquol DTPA: Denotes the pentasodium salt of diethylenetriaminepentaacetic acid, sold by the Company PROTEX.

Polychol 5: Denotes the oxyethyleneated lanoline fatty alcohol containing 5 mols of ethylene oxide, sold by the Company CRODA LTD.

Polychol 20: Denotes the oxyethyleneated lanoline fatty alcohol containing 20 mols of ethylene oxide, sold by the Company CRODA LTD.

Alfol C 16/18 E: Denotes the cetyl/stearyl alcohol sold by the Company CONDEA.

Lanette wax E: Denotes the sodium cetyl-/stearyl-sulphate sold by the Company HENKEL.

Cemulsol B: Denotes the oxyethyleneated castor oil sold by the Company RHONE POULENC Amphoteric compound I: Denotes the compound $$\underset{R-NH-CH-COONa}{CH_2-CO-NH-CH_2-CH_2-CH_2-N} \begin{matrix} C_2H_5 \\ \diagdown \\ C_2H_5 \end{matrix}$$

in which R represents the alkyl radicals of copra fatty acids.

Carbopol 934: Denotes the crosslinked polyacrylic acid sold by the Company GOODRICH CHEMICALS.

Complerlan KD: Denotes the copra diethanolamide sold by the Company HENKEL.

Blanose R 530: Denotes the sodium salt of carboxymethylcellulose.

Ethomeen O₁₂: Denotes the oxyethyleneated oleylamine containing 12 mols of ethylene oxide, sold by the Company ARMOON HESS CHEMICAL LTD.

Trilon B: Denotes ethylenediaminetetraacetic acid.

We claim:

1. A compound of the formula:

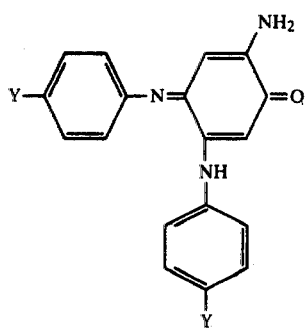

in which: Y represents (IV) 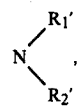

R'₁ and R'₂ independently of one another denoting an alkyl, mesylaminoalkyl, piperidinoalkyl or hydroxyalkyl group, the alkyl groups containing 1 to 6 carbon atoms, or a cosmetically acceptable salt thereof.

2. Compound according to claim 1 in which R'₁ and R'₂ denote hydroxyethyl.

3. A composition suitable for dyeing keratin fibers, comprising a compound according to claims 1 or 2 and a cosmetically acceptable carrier.

4. A process for dyeing keratin fibers, comprising applying thereto a compound according to claims 1 or 2 and a cosmetically acceptable carrier.

* * * * *